United States Patent
Wang et al.

(10) Patent No.: US 9,381,164 B2
(45) Date of Patent: *Jul. 5, 2016

(54) SILK NANOSPHERES AND MICROSPHERES AND METHODS OF MAKING SAME

(71) Applicant: TRUSTEES OF TUFTS COLLEGE, Medford, MA (US)

(72) Inventors: Xiaoqin Wang, Winchester, MA (US); David L. Kaplan, Concord, MA (US)

(73) Assignee: Trustees of Tufts College, Medford, MA (US)

(*) Notice: Subject to any disclaimer, the term of this patent is extended or adjusted under 35 U.S.C. 154(b) by 0 days.

This patent is subject to a terminal disclaimer.

(21) Appl. No.: 14/216,756

(22) Filed: Mar. 17, 2014

(65) Prior Publication Data

US 2015/0056293 A1 Feb. 26, 2015

Related U.S. Application Data

(63) Continuation of application No. 13/496,227, filed as application No. PCT/US2010/050698 on Sep. 29, 2010, now Pat. No. 8,715,740.

(60) Provisional application No. 61/246,676, filed on Sep. 29, 2009.

(51) Int. Cl.
*A61K 9/50* (2006.01)
*A61K 9/127* (2006.01)
(Continued)

(52) U.S. Cl.
CPC .............. *A61K 9/5169* (2013.01); *A61K 9/14* (2013.01); *A61K 9/1605* (2013.01);
(Continued)

(58) Field of Classification Search
CPC ...... A61K 9/14; A61K 9/1605; A61K 9/1647
See application file for complete search history.

(56) References Cited

U.S. PATENT DOCUMENTS

| 1,989,005 A | 1/1935 | Fink et al. |
| 4,233,212 A | 11/1980 | Otoi et al. |

(Continued)

FOREIGN PATENT DOCUMENTS

| CA | 2405850 A1 | 10/2002 |
| EP | 1440088 A2 | 7/2004 |

(Continued)

OTHER PUBLICATIONS

Agarwal, et al., Effect of Moisture Absorption on the Thermal Properties of Bombyx mori Silk Fibroin Films, Journal of Applied Polymer Science, 63(3):401-410 (1997).

(Continued)

*Primary Examiner* — Carlos Azpuru
(74) *Attorney, Agent, or Firm* — Choate, Hall & Stewart, LLP

(57) ABSTRACT

The present invention provides for methods of preparing silk nanoparticles and microparticles, methods of encapsulating an active agent into the silk nano- and microparticles and compositions comprising these silk particles. In particular, the silk spheres are prepared from phase separation of silk and polyvinyl alcohol (PVA), without exposure to an organic solvent. The method employs a chemical, PVA, which is an FDA-approved ingredient in drug formulations. Different parameters can be adjusted to control the size and shape of the silk spheres during the fabrication process. The silk particle compositions of the present invention may also encapsulate active agents or chemicals. Such compositions allow the active agents to be controllably and sustainably released to the target organs or tissues. The silk composition entrapping active agents also provides for a long-term storage medium for the active agents so entrapped. The silk nano- and microparticles of the present invention are thus suitable for a variety of biomedical and pharmaceutical applications, such as drug delivery or tissue engineering.

18 Claims, 6 Drawing Sheets

(51) Int. Cl.
*A61K 9/51* (2006.01)
*A61K 9/14* (2006.01)
*A61K 9/16* (2006.01)
*A61K 31/352* (2006.01)

(52) U.S. Cl.
CPC ............ *A61K 9/1647* (2013.01); *A61K 9/5052* (2013.01); *A61K 9/5089* (2013.01); *A61K 9/5192* (2013.01); *A61K 31/352* (2013.01); *Y10T 428/2982* (2015.01)

(56) References Cited

U.S. PATENT DOCUMENTS

| | | | |
|---|---|---|---|
| 4,820,418 | A | 4/1989 | Hirotsu et al. |
| 5,047,507 | A | 9/1991 | Buchegger et al. |
| 5,290,494 | A | 3/1994 | Coombes et al. |
| 5,606,019 | A | 2/1997 | Cappello |
| 5,728,810 | A | 3/1998 | Lewis et al. |
| 5,770,193 | A | 6/1998 | Vacanti et al. |
| 5,994,099 | A | 11/1999 | Lewis et al. |
| 6,110,590 | A | 8/2000 | Zarkoob et al. |
| 6,123,819 | A | 9/2000 | Peeters |
| 6,175,053 | B1 | 1/2001 | Tsubouchi |
| 6,592,623 | B1 | 7/2003 | Bowlin et al. |
| 6,815,427 | B2 | 11/2004 | Tsubouchi et al. |
| 6,902,932 | B2 | 6/2005 | Altman et al. |
| 7,041,797 | B2 | 5/2006 | Vollrath |
| 7,057,023 | B2 | 6/2006 | Islam et al. |
| 7,285,637 | B2 | 10/2007 | Armato et al. |
| 7,635,755 | B2 | 12/2009 | Kaplan et al. |
| 7,662,409 | B2 | 2/2010 | Masters |
| 7,674,882 | B2 | 3/2010 | Kaplan et al. |
| 7,727,575 | B2 | 6/2010 | Kaplan et al. |
| 7,842,780 | B2 | 11/2010 | Kaplan et al. |
| 7,868,146 | B2 | 1/2011 | Scheibel et al. |
| 7,960,509 | B2 | 6/2011 | Kaplan et al. |
| 8,071,722 | B2 | 12/2011 | Kaplan et al. |
| 8,715,740 | B2 * | 5/2014 | Wang ................... A61K 9/5169 264/4.1 |
| 2001/0006133 | A1 | 7/2001 | Nakamura |
| 2002/0028243 | A1 | 3/2002 | Masters |
| 2003/0007991 | A1 | 1/2003 | Masters |
| 2003/0183978 | A1 | 10/2003 | Asakura |
| 2004/0005363 | A1 | 1/2004 | Tsukada et al. |
| 2004/0266992 | A1 | 12/2004 | Migliaresi et al. |
| 2005/0260706 | A1 | 11/2005 | Kaplan et al. |
| 2007/0187862 | A1 | 8/2007 | Kaplan et al. |
| 2007/0212730 | A1 | 9/2007 | Vepari et al. |
| 2008/0085272 | A1 | 4/2008 | Kaplan et al. |
| 2008/0293919 | A1 | 11/2008 | Kaplan et al. |
| 2009/0171467 | A1 | 7/2009 | Mann et al. |
| 2009/0202614 | A1 | 8/2009 | Kaplan et al. |
| 2009/0232963 | A1 | 9/2009 | Kaplan et al. |
| 2009/0234026 | A1 | 9/2009 | Kaplan et al. |
| 2009/0297588 | A1 | 12/2009 | Rheinnecker et al. |
| 2010/0028451 | A1 | 2/2010 | Kaplan et al. |
| 2010/0046902 | A1 | 2/2010 | Kaplan et al. |
| 2010/0055438 | A1 | 3/2010 | Kaplan et al. |
| 2010/0063404 | A1 | 3/2010 | Kaplan et al. |
| 2010/0065784 | A1 | 3/2010 | Kaplan et al. |
| 2010/0068740 | A1 | 3/2010 | Kaplan et al. |
| 2010/0070068 | A1 | 3/2010 | Kaplan et al. |
| 2010/0095827 | A1 | 4/2010 | Rheinnecker et al. |
| 2010/0096763 | A1 | 4/2010 | Kaplan et al. |
| 2010/0120116 | A1 | 5/2010 | Kaplan et al. |
| 2010/0178304 | A1 | 7/2010 | Wang et al. |
| 2010/0191328 | A1 | 7/2010 | Kaplan et al. |
| 2010/0196447 | A1 | 8/2010 | Kaplan et al. |
| 2010/0292338 | A1 | 11/2010 | Rheinnecker et al. |
| 2011/0046686 | A1 | 2/2011 | Kaplan et al. |
| 2011/0076384 | A1 | 3/2011 | Cannizzaro et al. |
| 2011/0121485 | A1 | 5/2011 | Rheinnecker et al. |
| 2011/0135697 | A1 | 6/2011 | Omenetto et al. |
| 2011/0152214 | A1 | 6/2011 | Boison et al. |
| 2011/0171239 | A1 | 7/2011 | Kaplan et al. |
| 2012/0121820 | A1 | 5/2012 | Kaplan et al. |
| 2012/0123519 | A1 | 5/2012 | Lovett et al. |
| 2012/0187591 | A1 | 7/2012 | Wang et al. |

FOREIGN PATENT DOCUMENTS

| | | |
|---|---|---|
| GB | 1182153 A | 2/1970 |
| JP | 55-139427 | 10/1980 |
| JP | 56166235 | 12/1981 |
| JP | S58-38449 | 8/1983 |
| JP | 60-142259 A | 7/1985 |
| JP | 60-259677 | 12/1985 |
| JP | 01118544 | 11/1989 |
| JP | H02-109570 A | 4/1990 |
| JP | 04-263611 B2 | 9/1992 |
| JP | H06-346314 | 12/1994 |
| JP | 08-295697 | 11/1996 |
| JP | H10-036676 | 2/1998 |
| JP | 2000-273264 A | 10/2000 |
| JP | 2003-192807 A | 7/2003 |
| JP | 2004-018757 A | 1/2004 |
| JP | 2004-068161 A | 3/2004 |
| JP | 2008-502739 A | 1/2008 |
| KR | 10-2008-0044890 | 5/2008 |
| WO | WO-99/01089 A1 | 1/1999 |
| WO | WO-01/36531 | 5/2001 |
| WO | WO-01/55626 A1 | 8/2001 |
| WO | WO-02/072931 | 9/2002 |
| WO | WO-03/022909 A1 | 3/2003 |
| WO | WO-03/038033 A2 | 5/2003 |
| WO | WO-2004/000915 A2 | 12/2003 |
| WO | WO-2004/041845 A2 | 5/2004 |
| WO | WO-2005/012606 A2 | 2/2005 |
| WO | WO-2005/123114 A2 | 12/2005 |
| WO | WO-2008/118133 A2 | 10/2008 |
| WO | WO-2008/127405 A2 | 10/2008 |
| WO | WO-2009/156226 A2 | 12/2009 |
| WO | WO-2011/006133 A2 | 1/2011 |

OTHER PUBLICATIONS

Altman, G. H. et al., Silk-based biomaterials, Biomaterials, 24:401-416 (2003).
Ando, et al., Piezoelectric and Related Properties of Hydrated Silk Fibroin, Reports on Progress in Polymer Physics in Japan, XXIII:775-778 (1980).
Asakura, T. et al., Conformational characterization of Bombyx mori silk fibroin in the solid state by high-frequency carbon-13 cross polarization-magic angle spinning NMR, x-ray diffraction, and infrared spectroscopy, Macromolecules, 18(10):1841-1845 (1985).
Asakura, T. et al., NMR of silk fibroin 2. 13C NMR study of the chain dynamics and solution structure of Bombyx mori silk fibroin, Macromolecules, 17:1075-1081 (1984).
Chen et al., pH sensitivity and ion sensitivity of hydrogels based on complex-forming chitosan/silk fibroin interpenetrating polymer network, J. Appl. Polymer Sci., 65:2257-62 (1997).
Chen et al., Separation of alcohol-water mixture by pervaporation through a novel natural polymer blend membrane-chitosan/silk fibroin blend membrane, J. Appl. Polymer Sci., 73:975-980 (1999).
Chen, X. et al., Conformation Transition Kinetics of Bombyx mori Silk Protein, Proteins: Structure, Function, and Bioinformatics, 68:223-231 (2007).
Demura, M. et al., Immobilization of Biocatalysts with Bombyx mori Silk Fibroin by Several Kinds of Physical Treatment and Its Application to Glucose Sensors, Biosensors, 4(6):361-372 (1989).
Demura, M., Porous membrane of Bombyx mori silk fibroin: structure characterization, physical properties and application to glucose oxidase immobilization, Journal of Membrane Science, 59:32-52 (1991).
Derwent Record, Abstract of JP 08295697 A2, Production of Aqueous Solution of Silk Fibroin At High Concentration (Nov. 12, 1996).
Doshi et al., Electrospinning Process and Applications of Electrospun Fibers, J/Electrostatics, 35: 151-160 (1995).
Extended European Search Report for EP 10821161.6, 7 pages (Sep. 17, 2013).

(56) References Cited

OTHER PUBLICATIONS

Freddi G. et al., Silk fibroin/cellulose blend films: preparation, structure, and physical properties, J Appl Polymer Sci, 56:1537-1545 (1995).

Hijirida et al., 13C NMR of Nephila clavipes Marjo Ampullate Silk Gland, Biophysical Journal 71:3442-3447 (1996).

Hinman, M.B. et al., Synthetic spider silk: a modular fiber, Trends Biotechnol, 18(9):374-9 (2000).

Horan, RL et al., In vitro degradation of silk fibroin, Biomaterials, 26(17): 3385-93 (2005).

Hu, X. et al., Regulation of Silk Material Structure by Temperature-Controlled Water Vapor Annealing, Biomacromolecules, 12:1686-1696 (2011).

Huang et al., Engineered collagen-PEO nanofibers and fabrics, J Biomater Sci Polymer Edn, 12(9):979-993 (2001).

Huang et al., Generation of Synthetic Elastin-Mimetic Small Diameter Fibers and Fiber Networks, Macromolecules, 33:2989-2997 (2000).

International Search Report for PCT/US2010/050698, 4 pages (Jun. 30, 2011).

Jin, H.J. and Kaplan, D.L., Mechanism of silk processing in insects and spiders, Nature, 424(6952):1057-1061 (2003).

Jin, H.J. et al., Electrospinning Bombyx mori silk with poly(ethylene oxide), Biomacromolecules, 3(6):1233-9 (2002).

Jin, H.J. et al., Water-Stable Silk Films with Reduced β-Sheet Content, Advanced Functional Materials, 15:1241-1247 (2005).

Kim et al., Structure and Properties of Silk-Hydrogels, Biomacromolecules, 5(3):786-792 (2004).

Kweon et al., Preparation of Semi-Interpreting Polymer Networks Composed of Silk Fibroin and Poly( ethylene glycol) Macromer, J. Appl. Polymer Sci., 80:1848-1853 (2001).

Lammel, A. et al., Processing conditions for the formation of spider silk microspheres, ChemSusChem., 1(5):413-6 (2008).

Lazaris, A. et al., Spider silk fibers spun from soluble recombinant silk produced in mammalian cells, Science. 295(5554):472-6 (2002).

Li, et al., Electrospun Silk-BMP-2 scaffolds for Bone Tissue Engineering, Biomaterials, 27:3115-3124 (2006).

Liang, C. X., et al., Improvements of the physical properties of fibroin membranes with sodium alginate, J. Appl. Polymer Sci., 1937-1943 (1992).

Liebmann, B. et al., Formulation of poorly water-soluble substances using self-assembling spider silk protein, Colloids and Surfaces A: Physicochem. Eng. Aspects 331:126-132 (2008).

Lu, Q. et al., Water-insoluble silk films with silk I structure, Acta Biomaterialia, 6(4):1380-1387 (2010).

Megeed et al., Controlled Release of Plasmid DNA from a Genetically Engineered Silk-Elastin like Hydrogel, Pharmaceutical Research, 19(7):954-959 (2002).

Myung, S.J. et al., Fluorescent silk fibroin nanoparticles prepared using a reverse microemulsion, Macromolecular Research, 16(7):604-608 (2008).

Nazarov, et al., Porous 3-D Scaffolds from Regenerated Silk Fibroin, Biomacromolecules, 5:718-726 (2004).

Numata, et al., Silk-based Delivery Systems of Bioactive Molecules, Advances in Drug Delivery Reviews, 62(15):1497-1508 (2010).

Petrini et al., Silk fibroin-polyurethane scaffolds for tissue engineering, Journal of Materials Science: Materials in Medicine, 12:849-853 (2001).

Reneker D.H. and Chun, I., Nanometre diameter fibres of polymer, produced by electrospinning, Nanotechnology, 7:216-223 (1996).

Sawyer et al., Dextran therapy in thrombophlebitis. Abstract, JAMA, 191(9):740-742 (1965).

Sofia et al. Functionalized Silk-Based Biomaterials for Bone Formation, J. Biomed. Mater. Res. 54:139-148 (2001).

U.S. Appl. No. 60/906,509, by Omenetto et al. filed Mar. 13, 2007.

U.S. Appl. No. 61/224,618, by Numata et al. filed Jul. 10, 2009.

Wang, et al., Silk Microspheres for Encapsulation and Controlled Release, Journal of Controlled Release, 117(3):360-370 (2006).

Wang, X. et al., Biomaterial Coatings by Stepwise Deposition of Silk Fibroin, Langmuir, 21(24): 11335-11341 (2005).

Wang, X. et al., Silk nanospheres and microspheres from silk/pva blend films for drug delivery, Biomaterials, 31(6): 1025-1035 (2010).

Wenk, et al., Silk Fibroin as a Vehicle for Drug Delivery in Tissue Regeneration, Dissertation Eth. No. 18659 (2009).

Wenk, et al., Silk Fibroin Spheres as a Platform for Controlled Drug Delivery, Journal of Controlled Release, 132(1):26-34 (2008).

Wilz, A. et al., Silk Polymer-based Adenosine Release: Therapeutic Potential for Epilepsy, Biomaterials, 29(26):3609-3616 (2008).

Written Opinion for PCT/US2010/050698, 5 pages (Jun. 30, 2011).

Yamada et al., AFM observation of silk fibroin on mica substrates: morphologies reflecting the secondary structure, Thin Solid Films, 440:208-16 (2003).

Yeo, et al., Simple Preparation and Characteristics of Silk Fibroin Microsphere, European Polymer Journal, 39:1195-1199 (2003).

Zhang, Y-Q et al., Formation of silk fibroin nanoparticles in water-miscible organic solvent and their characterization, Journal of Nanoparticle Research, 9(5):885-900 (2007).

Zhou et al., Preparation of a novel core-shell nanostructured gold colloid-silk fibroin bioconjugate by the protein in situ redox technique at room temperature, Chem Commun, 2518-2519 (2001).

* cited by examiner

SILK NANOSPHERES AND MICROSPHERES AND METHODS OF MAKING SAME

CROSS REFERENCE TO RELATED APPLICATIONS

This application is a continuation of U.S. patent application No. 13/496,227, filed Apr. 11, 2012, now U.S. Pat. No. 8,715,740, which is the National Stage Application PCT/US2010/050698, filed Sep. 29, 2010 which claims the benefit of U.S. Provisional Application No. 61/246,676 filed Sep. 29, 2009, the entire contents of each of which is incorporated herein by reference.

GOVERNMENT SUPPORT

This invention was made with government support under grant No. P41 EB002520 awarded by the NIH Tissue Engineering Resource Center. The U.S. government has certain rights in the invention.

FIELD OF THE INVENTION

The present invention relates to compositions and methods for preparing silk nanoparticles and microparticles with controllable size and shape, and methods of encapsulating active agent into silk nano- and microparticles. In particular, silk spheres of several embodiments are prepared from phase separation of silk/polyvinyl alcohol (PVA), without exposure to an organic solvent. The silk particles of the present invention are suitable for a variety of biomedical and pharmaceutical applications, such as drug delivery systems, storage media, tissue engineering, or enzyme analysis.

BACKGROUND OF THE INVENTION

Micro- and nano-particulate systems have been used widely in various biomedical and pharmaceutical applications, such as drug delivery. Depending on the delivery route and disease site, either microspheres (1 µm-1000 µm) or nanospheres (1 nm-1000 nm) provide suitable delivery systems. For example, nanospheres can be designed as short-acting delivery vehicles and used to induce efficient drug accumulation at a target site, for example, to target a tumor in cancerous tissues. Microspheres can be used as depot drug carriers for long-acting delivery. For example, microvesicles may be used for tissue regeneration by releasing growth factors in a polymeric scaffold.

Synthetic materials, such as biodegradable synthetic polymers, have been used to fabricate micro- and nano-particulate delivery systems. Many of these polymers, however, have inherent limitations for tissue engineering and drug delivery applications. For example, organic solvent is usually needed to dissolve these polymers because of their hydrophobic nature, and the organic solvent may be detrimental to the proteins or other active agents to be loaded in/on the particles. Moreover, the degradation products of many of these polymers are acidic, which may cause the denaturation of proteinaceous or other acid-sensitive drugs. Hence, there remains a need for active agents and processes that provide for microspheres and nanospheres with controllable sphere size and shape, and that avoid using organic solvents and other harsh conditions during the fabrication process.

SUMMARY

The present embodiments provide methods of preparing silk nanoparticles and microparticles, methods of encapsulating an active agent into the silk nanoparticles and microparticles, and compositions comprising these silk particles. In particular, water-insoluble silk spheres may be prepared from dissolving the silk/polyvinyl alcohol (PVA) blend films in an aqueous solution, without exposure to an organic solvent at any stage in production. PVA is an FDA-approved ingredient in drug formulations. Different parameters can be adjusted to control the size and shape of the silk micro- and nanoparticles during the fabrication process. The silk micro- and nanoparticle compositions of the present invention may also comprise silk spheres encapsulating an active agent(s) or chemical(s), and such compositions allow the active agents to be controllably and sustainably released to target cells, organs, or tissues. The methods of the present invention are thus easy, safe, controllable, time and energy efficient, and drug-amenable. The silk nanospheres and microspheres of the present invention are suitable for a variety of biomedical and pharmaceutical applications, such as drug delivery system, storage medium, or tissue engineering.

The embodiments of the present invention provide for methods of preparing silk spheres with the size of the spheres ranging from nanometers to micrometers. In one embodiment, the method comprises (a) mixing an aqueous silk fibroin solution with an aqueous PVA solution; (b) drying the solution of step (a) to form a film; (c) dissolving the film in water; and (d) removing at least a portion of the PVA, thereby forming silk spheres. Because no harsh conditions, such as shearing and heating, are involved in the sphere preparation process, the chemistry-based methods of the present invention are suitable for protein drug delivery applications. Depending on the intended use of the sphere, either nanospheres or microspheres may be produced and recovered by adjusting, for example, the concentrations or ratios of the silk fibroin solution and the PVA solution. Indeed, using the methods of the present invention, the shape, size and size distribution of silk particles can be controlled by various means.

Some embodiments of the present invention thus provide for methods of preparing silk spheres with the size of the spheres ranging from nanometers to micrometers, comprising the steps of (a) providing an aqueous silk fibroin solution; (b) providing an aqueous PVA solution, wherein the PVA has an average molecular weight of 30,000-124,000; (c) mixing the silk fibroin solution and PVA solution to form a blend solution, wherein the concentration of silk in the blend solution is up to 15 wt %, and the concentration of PVA in the blend solution is about equal to or up to about 4-times-higher than the concentration of silk in the blend solution; (d) drying the blend solution to form a film; (e) dissolving the film in water; and (f) removing at least a portion of the PVA, thereby forming silk microspheres and nanospheres.

Silk microspheres within a narrower size distribution may be obtained by adjusting one or more parameters as discussed herein. For example, silk microspheres with a size ranging from about 5 µm to about 10 µm may be obtained by, for example, adjusting the concentrations of silk fibroin and PVA in the blended solution; or sonicating the silk/PVA blend solution (for example, with an energy output of about 4 watts) before casting and drying the blend solution to form films.

Another embodiment of the present invention provides for a method of preparing silk nanospheres with at least one of the following properties: the mean sphere size less than about 500 nm; the polydispersity index (PDI) is below 0.3; or no spheres larger than 2 µm; this approach comprising (a) providing an aqueous silk fibroin solution; (b) providing an aqueous PVA solution, wherein the PVA has an average molecular weight of 30,000-124,000; (c) mixing the silk fibroin solution and PVA solution to form a blend solution, wherein the concentration of silk in the blend solution is up to about 0.04 wt % silk and the concentration of PVA in the blend solution is up to about 0.16 wt %; (d) drying the blend solution to form a film; (e) dissolving the film in water; and (f) removing at least a portion of the PVA, thereby forming silk nanospheres.

Yet another embodiment of the present invention provides for a method of preparing silk nanospheres with the mean sphere size of the nanospheres less than about 330 nm, PDI below 0.4, and/or no spheres larger than about 2 µm, by (a) providing an aqueous silk fibroin solution; (b) providing an aqueous PVA solution, wherein the PVA has an average molecular weight of 30,000-124,000; (c) mixing the silk fibroin solution and PVA solution to form a blend solution, wherein the concentration of silk in the blend solution is up to 15 wt %, and the concentration of PVA in the blend solution is about 4-times the concentration of silk in the blend solution; (d) sonicating the blend solution; (e) drying the sonicated solution to form a film; (f) dissolving the film in water; and (g) removing at least a portion of the PVA, thereby forming the silk spheres nanospheres less than about 330 nm and no spheres larger than about 2 µm.

According to the embodiments of the present invention, silk microparticles and nanoparticles with variant shapes may be obtained. Following the methods of the present invention, silk microspheres or nanospheres are formed in the silk/PVA blend film. Before dissolving the film in water, constraints, such as physical forces, may be applied on the silk/PVA blend film to change the shape of silk particles in the blend films. For example, spindle-shaped silk particles can be obtained by simply stretching the dried silk/PVA blend films, thus converting the silk microspheres or nanospheres into spindle-shaped microparticles or spindle-shaped nanoparticles. In another example, water vapor (water-annealing) treatment of the silk/blend film may result the silk particles in a flattened disk shape. Uniform silk microparticles or nanoparticles (such as spindle-shaped particles or flattened disk-shaped particles) may be obtained by adjusting the particle size and size distribution of silk microspheres or nanospheres in the blend film before applying constraints. Other physical forces, such as compressing and twisting, can also generate silk particles with other different shapes.

The embodiments of the present invention also provide for methods of encapsulating an active agent (such as an antibody, drug, or small molecule) in porous silk nanospheres or microspheres, or spheres with the size of the spheres ranging from nanometers to micrometers, comprising the steps of (a) mixing an aqueous silk fibroin solution and an active agent with a PVA solution; (b) drying the solution to form a film; (c) dissolving the film in water; and (d) removing at least a portion of the PVA, thereby forming the active agent-encapsulated silk spheres.

DESCRIPTION OF THE DRAWINGS

FIGS. 1A-1D are silk microspheres and nanospheres collected from silk/PVA blend films after the steps of film dissolution, centrifugation, washing and drying. The silk spheres were washed once after the step of film dissolution for FIGS. 1A and 1B, washed once followed by the treatment of 50% MeOH for 24 hr for FIG. 1C, and washed three times for FIG. 1D. The inset in FIG. 1D shows a silk microsphere with a porous interior structure. FIG. 1E shows silk microspheres treated with 50% (v/v) MeOH for 15 hr. The spheres were centrifuged and washed once with water. FIGS. 1F and 1G present silk spheres prepared from water-annealed silk/PVA blend films. FIGS. 1H and 1I shows spindle-shaped silk particles prepared by stretching the silk/PVA blend films before dissolution. The inset in FIG. 1H shows the exposed interior structure of some spheres, likely caused during film stretching. Scale bar is 10 µm in FIGS. 1A and 1H; 1 µm in FIGS. 1B, 1C, and 1D; and 2 µm in FIGS. 1E, 1F, 1G, and 1I to show the detailed surface morphology of individual silk particles.

FIGS. 3A, 3B, 3D, and 3E depict that silk spheres prepared from a 1.0% silk/4.0% PVA (wt %) blend solution were dominated by silk microspheres with a size ranging from 1 µm-30 µm. Silk spheres prepared from a 0.20% silk/0.80% PVA (wt %) blend solution were dominated by silk microspheres with a size ranging from 1 µm-30 µm. FIGS. 3C and 3F show that silk spheres prepared from a 0.04% silk/0.16% PVA (wt %) blend solution were dominated by silk nanospheres with a size lower than 400 nm. FIGS. 3A-3C are images with low magnification; FIGS. 3D-3F are images with high magnification. Scale bar is 10 µm in FIGS. 3A and 3B; 1 µm in FIG. 3C to show multiple nanospheres; 2 µm in FIGS. 3D and 3E; and 200 nm in FIG. 3F to show detailed structure of nanospheres.

FIGS. 6A-6F show confocal images of the spheres suspended in aqueous solution. FIGS. 6A-6C are low magnification images; FIGS. 6D-6F are high magnification images. The table below the images shows the amount of drug loaded and the loading efficiency determined by measuring the amount of drug remained in the supernatant fractions after centrifugation. Scale bar is 35 µm in FIGS. 6A-6C; and 5 µm in FIGS. 6D-6F.

FIG. 9A shows the probability densities (G(Dh), solid lines) and cumulative distributions (C(Dh), dashed lines) of silk spheres obtained from blending silk and PVA solutions each with an initial concentration at 0.2 wt %, 1 wt % and 5 wt %, respectively, with a blending ratio of 1:4, using the cumulant analysis. The final weight concentrations of silk/PVA in the blend solution were 0.04% silk/0.16% PVA, 0.2% silk/0.8% PVA, and 1.0% silk/4.0% PVA, respectively. FIG. 9B shows the hydrodynamic size distributions obtained from the same samples as in FIG. 9A using intensity-averaged exponential sampling.

DETAILED DESCRIPTION

Figure 1:
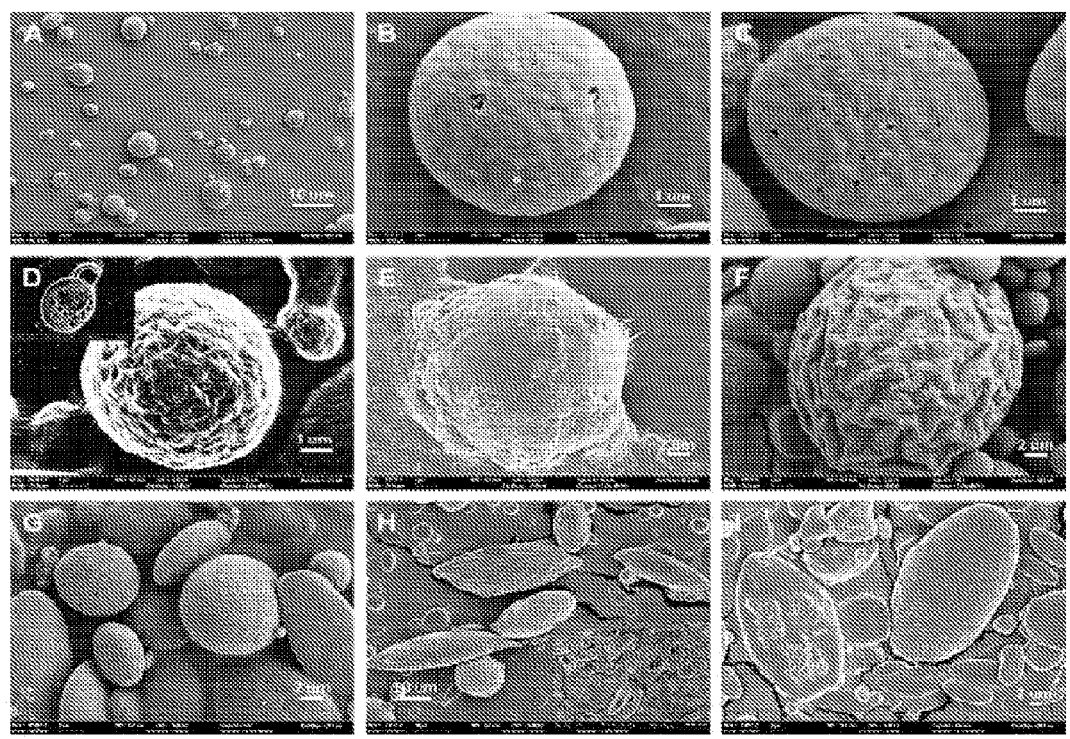
FIGS. 1A-1I are scanning electron micrographs of silk spheres prepared from silk/PVA blend solutions containing 1.0% silk and 4.0% PVA (wt %).

It should be understood that this invention is not limited to the particular methodology, protocols, and reagents, etc., described herein and as such may vary. The terminology used herein is for the purpose of describing particular embodiments only, and is not intended to limit the scope of the present invention, which is defined solely by the claims.

As used herein and in the claims, the singular forms include the plural reference and vice versa unless the context clearly indicates otherwise. Other than in the operating examples, or where otherwise indicated, all numbers expressing quantities of ingredients or reaction conditions used herein should be understood as modified in all instances by the term "about."

All patents and other publications identified are expressly incorporated herein by reference for the purpose of describing and disclosing, for example, the methodologies described in such publications that might be used in connection with the present invention. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents is based on the information available to the applicants and does not constitute any admission as to the correctness of the dates or contents of these documents.

Unless defined otherwise, all technical and scientific terms used herein have the same meaning as those commonly understood to one of ordinary skill in the art to which this invention pertains. Although any known methods, devices, and materials may be used in the practice or testing of the invention, the methods, devices, and materials in this regard are described herein.

Micro- and nanoparticulate systems have been widely used in various biomedical and pharmaceutical applications. Chiellini et al., 3 Nanomed. 367-93 (2008). For drug delivery purposes, the systems serve as a reservoir of therapeutic agents, with a spatial and temporal control of drug release profiles, thus providing for desirable therapeutic outcomes. The micro- and nano spheres used should generally have the ability to incorporate a drug without damaging it, tunable drug release kinetics, high in vivo stability, biocompatibility (e.g., lack of toxicity and immunogenicity), and the potential to target specific organs and tissues. Depending on the delivery route and disease site, either microparticles (1 µm-1000 µm) or nanoparticles (1 nm-1000 nm) may be suitable.

Nanoparticles can penetrate small capillaries, overcome numerous physiological barriers, and can be taken up by cells. Hence, nanospheres can be used to induce efficient drug accumulation at the target sites. Efforts have been made to develop drug-delivery nanospheres for treating various diseases, such as cancer, to obtain a more targeted localization in tumors and more active cellular uptake. Davis et al., 7 Nat. Rev. Drug Discov. 771-82 (2008). Nanospheres are usually designed as short-acting delivery vehicles and are administrated via different routes: intravenous, intramuscular, subcutaneous, oral, nasal, ocular, or transdermal. Generally, nanospheres are either fluidized with a liquid carrier or administered as a solid powder. Hoet et al., 2 J. Nanobiotech. 12 (2004); Mundargi et al., 125 J. Control Release 193-209 (2008).

Microspheres are generally used as depot drug carriers for long-acting delivery and are often administered intramuscularly or subcutaneously. Mundargi et al., 2008. Microspheres possessing mucoadhesive properties can also be delivered orally or nasally. Such microspheres can adhere to the mucous membrane, and can release the encapsulated drug over a long period of time. Mundargi et al., 2008. Usually, the drug release of long-acting drug delivery vehicles is controlled based on the diffusion of drug molecules through polymer network and/or degradation (hydrolysis or proteolysis) of the polymer matrix. Long-acting delivery microvesicles may also be used for tissue regeneration by releasing growth factors in a polymeric scaffold. Chen & Mooney, 20 Pharm. Res. 1103-12 (2003). Microvesicles are incorporated in the scaffold and distributed preferably in a desired pattern, so that the encapsulated growth factors are released in a controllable manner both spatially and temporally. Wang et al., 134 J. Control. Release 81-90 (2009).

In some cases, nano spheres have been incorporated into larger spheres by flocculation, spray drying, or other means, so that the spheres prepared may have a desirable size to target a specific disease site, such as the case in pulmonary drug delivery. Rytting et al., 5 Expert Opin. Drug Deliv. 629-39 (2008). Nanospheres can also be microencapsulated using enteric coatings for controlling the release and degradation in vivo. Lee et al., 20 J. Microencapsul. 489-96 (2003). The shape of spheres may have some impacts on the polymer degradation, thus affecting the drug release profiles. Champion et al., 121 J. Control. Release 3-9 (2007).

Synthetic materials can be used to fabricate micro- and nanoparticulate delivery systems. For example, polyesters and polyanhydrides are commonly used as biodegradable synthetic polymers. Chiellini et al., 2008. Because these polymers are composed of single monomers, their in vivo degradation can be well-controlled, and in some cases can be predicated by factors like molecular weights, ratios between different copolymers, and the degree of crystallinity, etc. These polymers, however, often have inherent shortcomings that can limit their applications. For example, these polymers need to be dissolved in organic solvents because of the hydrophobic nature. The organic solvent may be detrimental to the protein drugs to be loaded. Moreover, the degradation products of these polymers are often acidic, which may denature proteinaceous active agents.

Compared with synthetic polymers, naturally derived degradable polymers, such as collagen, gelatin, cellulose, hyaluronic acid, alginate and chitosan, are advantageous in many aspects. For example, these natural polymers are naturally abundant, have good biocompatibility, and the ability to be modified readily by simple chemistry. Chiellini et al., 2008; Dang & Leong, 58 Adv. Drug Delivery 487-99 (2006). Using these natural polymers for biomedical applications is often difficult, however, usually because of their inconsistent batch qualities, instability, and uncontrollable degradation rates.

Silkworm fibroin is the structural protein of silk fibers. Silk fibroin proteins, particularly the one from *Bombyx mori* (the commercialized source of silk for textiles via sericulture), have been investigated as a active agent for tissue engineering and drug delivery. Altman et al., 24 Active agents 401-16 (2003); Hofmann et al., 111 J. Control. Release 219-27 (2006); Wang et al., 117 J. Control. Release 360-70 (2007); Wang et al., 29 Biomats. 1054-64 (2008); Wenk et al., 132 J. Control. Release 26-34 (2008). See, also, e.g., WO 04/000, 915; WO 04/062,697; WO 05/012,606; WO 08/150,861. Silk fibroin can be fabricated easily into desired shapes, such as films, 3-D porous scaffolds, electrospun fibers, and hydrogels. Silk fibroin solutions may be prepared as aqueous stock solution in accordance with the procedures used previously. Sofia et al., 54 J. Biomed. Mat. Res. 139-48 (2001). Silk fibroin proteins represent a unique family of natural fibrous proteins due to their unique structure and the resulting functions. Altman et al., 2003; Kaplan et al., 544 Silk Polymers: Mats. Sci. & Biotech. (Am. Chem. Soc'y Symp. Series, Washington, D.C., 1994). The molecular structure of silks often comprises large regions (blocks) of hydrophobic amino acids, segregated by relatively short and more hydrophilic regions (spacers). The hydrophobic domains assemble into protein crystals ($\beta$-sheets). These $\beta$-sheets form physical crosslinks to stabilize the silk structure, and are generally dominated by repeats of alanine, glycine-alanine, or glycine-alanine-serine amino acid residues. The pI of silk is around 4, with the charged amino acids located mostly in the hydrophilic regions as well as the N- and C-termini. Bini et al., 335 J. Mol. Biol. 27-40 (2004).

Compared with other naturally degradable materials, silk fibroin exhibits superior mechanical properties, tunable in vivo degradation rates ranging from weeks to months due to a controllable level of crystallinity, excellent biocompatibility with no inflammatory and immunogenic response after implantation, ability to be processed into materials in an aqueous phase, and diverse material formats including films, fibers, gels, sponges, microspheres, etc. Silk materials exhibit a high encapsulation efficiency and controllable drug release kinetics due to the controllable formation of crystalline $\beta$-sheet, and are thus suitable for drug delivery, particularly protein drugs. Hofmann et al., 2006; Wang et al., 2007; Wilz et al., 29 Biomats. 3609-16 (2008). Therefore, silk fibroin protein-based micro- and nanoparticles provide new options for drug delivery due to their biocompatibility, biodegradability and their tunable drug loading and release properties.

Several techniques are available for the preparation of drug-loaded micro- and nanospheres, such as emulsion-solvent evaporation/extraction methods, solvent displacement, phase separation, self-assembling, rapid expansion of supercritical fluid solution, and spray drying. Silk fibroin has been fabricated into microspheres by various means and has been used for drug deliveries. Wang et al., 117 J. Control. Release 360-70 (2007); Gobin et al., 1 Int'l J. Nanomed. 81-87 (2006); Wang et al., 28 Biomats. 4161-69 (2007). See also, WO 08/118,133. Some previous fabrication methods, however, relied on organic solvents such as methanol, ethanol and acetone to induce silk fibroin crystalline $\beta$-sheet structure formation, thus making the silk spheres insoluble to water. Moreover, fabrication of silk nanospheres is still a challenging area. Although fabrication of silk nanospheres with a size ranging from 35 nm-125 nm has been reported recently, such fabrication method employs at least 70% (v/v) water-miscible protonic and polar aprotonic organic solvents. Zhang et al., 9 J. Nanosphere Res. 885-900 (2007). The nanospheres prepared by this method may be useful in cosmetics and anti-UV skincare products, but, they may not be suitable for drug delivery applications because of the use of organic solvents.

Fabrication of silk is usually difficult to control because of its high molecular weight and protein nature. Further, silk tends to self-assemble into fibers or gel networks upon heating, salting, high shearing, and changing pH values. In addition, controlling the size and shape of the silk spheres by the traditional fabrication methods was limited. Therefore, a new strategy is needed for the delivery of labile and active molecules to fabricate silk micro- and nanospheres with controllable sphere size and shape, and to avoid using organic solvents and other harsh conditions during the fabrication process.

It has been reported that phase separation between polyvinyl alcohol (PVA) and silk may occur spontaneously when the two polymer solutions were mixed and subsequently casted into films. Yamaura et al., 41 J. Appl. Polym. Sci. 2409-25 (1990); Tanaka et al., 42 Polym. Int. 107-11 (1997). Blending PVA and silk impacted the silk secondary structures as well as the mechanical and swelling properties of the blend films; and varying the molecular weights of PVA and the ratio between PVA and silk changed the macro- and microphase separation. Yamaura et al., 1990; Tanaka et al., 1997; Liu et al., 33 J. Macromol. Sci.: Pure Appl. Chem. 209-19 (1996); Tanaka et al., 45 Polym. Int. 175-84 (1998). In contrast, the present invention provides for silk micro- and nanospheres prepared from the phase separation of silk and PVA. In particular, the present invention provides for methods of preparing silk micro- and nanoparticles with controlled size and shape, and methods of encapsulating drugs into silk fibroin micro- and naoparticles. The drug loading and release profiles of drug-encapsulated silk spheres are also characterized.

The present invention provides for methods of preparing silk micro- and nanospheres with controlled sizes and shapes. The methods comprise using PVA as a continuous phase to separate silk fibroin solution into silk nanospheres and/or microspheres, either in silk/PVA blend solutions or in silk/PVA blend films. Silk micro- or nanospheres can be obtained and isolated easily by dissolving a dried blend film in water and then centrifuging to remove the residual PVA. The resulting silk micro- and nanospheres are water-insoluble and contain increased $\beta$-sheet content. The shape of the silk particles can be changed by applying constraints on the dried silk/PVA blend film before dissolving it in water. For example, spindle-shaped silk particles can be obtained by simply stretching the dried silk/PVA blend films. Sphere size and size distribution of the silk spheres of the present invention can be controlled by various means, such as varying the concentrations of silk and PVA in blend solution, or applying ultrasonication to the silk/PVA blend solution before drying the solution. The porous interior space and amphiphilic nature of the silk micro- or nanospheres facilitate the entrapment of drugs with different molecular weights and hydrophobicities, thus rendering the drug release under a controllable manner. The fabrication methods of the present invention, therefore, are easy, safe, controllable, time and energy efficient, drug-amenable, and are useful in making silk-based compositions suitable for a variety of biomedical and pharmaceutical applications, such as drug delivery or tissue engineering.

As used herein, the term "fibroin" includes silkworm fibroin and insect or spider silk protein. Lucas et al., 13 Adv. Protein Chem. 107-242 (1958). For example, fibroin is obtained from a solution containing a dissolved silkworm silk or spider silk. The silkworm silk protein is obtained, for example, from *B. mori*, and the spider silk is obtained from *Nephila clavipes*. In the alternative, suitable silk proteins can be obtained from a solution containing a genetically engineered silk, such as from recombinant bacteria, yeast, mammalian cells, transgenic animals, or transgenic plants. See, e.g., WO 97/08315; U.S. Pat. No. 5,245,012.

Silk/PVA blend films have been characterized previously in terms of mechanical properties, swelling, and permeability. Wang et al., 2007; Zhang et al., 2007; Yamaura et al., 1990; Tanaka et al., 1997. Silk and PVA were macroscopically or microscopically separated into different phases in the blend film, and the phase separation was dependent on the ratio between silk and PVA as well as the molecular weight of PVA used. When the silk fibroin is less than 50 wt % in the blend film, it formed microspheres with the size of the spheres distributing from less than 1 μm to about 30 μm. Zhang et al., 2007. The present invention further provides for the processing of the silk/PVA blend films to prepare uniform silk microspheres, nanospheres, microspindles or nanospindles under mild conditions.

In the present invention, PVA is used as a continuous phase to separate silk fibroin solution into silk spheres. Without being bound by theory, phase separation between silk and PVA is likely to occur immediately after mixing the silk and PVA starting solutions. To isolate silk spheres from aqueous blend solution, various means may be applied to the silk/PVA blend solution to make silk spheres water insoluble and hence separate the water-insoluble silk spheres from the aqueous phase. For example, the silk/PVA blend solution may be dried into film or treated with methanol.

In some embodiments of the present invention, silk fibroin and PVA are mixed in an aqueous solution, then cast and dried to form a silk/PVA blend film. The silk/PVA blend film is then dissolved in water to form silk microspheres that remain the same shape and size in water as appeared in the film. The silk spheres are readily collected and resuspended in water for characterization. In one embodiment, silk/PVA blend solution with 1.0 wt % of silk and 4.0 wt % of PVA may be prepared, for example, by mixing 5 wt % silk starting solution and 5 wt % PVA starting solution at a weight ratio of 1:4 silk:PVA. In another embodiment, silk/PVA blend solution with 2.5 wt % of silk and 2.5 wt % of PVA may be prepared, for example, by mixing 5 wt % silk starting solution and 5 wt % PVA starting solution at a weight ratio of 1:1 silk:PVA. Silk spheres prepared from the blend solutions in these embodiments have sizes ranging from about 1 μm to about 30 μm, and may be characterized by light microscope. These spheres are stable even after incubation of several weeks at room temperature. Under SEM, silk/PVA samples prepared from both blend solutions) contained micro- and nanospheres. The surfaces of the spheres were rough with some nanometer-sized pores (FIGS. 1A, 1B). Fifty percent (50%) methanol treatment did not change the morphology of the spheres (FIG. 1C). When the spheres were washed twice with water, the surface became more porous, perhaps due to a complete removal of PVA (FIG. 1D). Some spheres had defects and showed an empty interior space sustained by silk nanofibers (FIG. 1D inset). Such a surface morphology and interior porous structure may endow silk spheres with unique drug loading and release properties. Comparing the silk/PVA blend films prepared from the 2.5% silk/2.5% PVA (wt %) blend solution with that prepared from the 1.0% silk/4.0% PVA (wt %), the latter can quickly (within 10 minutes) and completely dissolve in water to form a homogeneous suspension, and the microspheres formed from the latter have a narrower size distribution as characterized by both the light microscopy and SEM.

Drying the blend solution into a film is a necessary step of forming stable water-insoluble silk nano- and microparticles. For example, in a control experiment, when a silk/PVA blend solution was stirred for 2 hours at room temperature (the condition used to prepare the blend films) followed by an immediate centrifugation, silk microspheres could not be collected. Other drying approaches, such as spray drying, may be used as alternatives, but may be more time and labor efficient than casting films. Methanol (or ethanol) and water vapor (water-annealing) treatment have been used to make as-cast silk films water-insoluble. Jin et al., 15 Adv. Funct. Mater. 1241-47 (2005). In the present embodiments, when methanol was added to the silk/PVA blend solutions and when methanol reached a concentration higher than 50% (v/v), stable and water-insoluble silk nano- and microspheres also formed in solution (FIG. 1E). The spheres prepared from methanol-treated silk/PVA blend solution, however, were accompanied with many silk fibroin aggregates, which were not observed in the preparation from the blend film. When the silk/PVA blend films were treated with water vapor under vacuum environment for 24 hours at room temperature, the film was still soluble in water, and some of the silk spheres formed exhibited a wrinkled surface (FIG. 1F) and/or a flattened disk shape (FIG. 1G).

The structures of silk spheres prepared from different treatments of silk/PVA blend solution are also evaluated. To determine the β-sheet content, fourier transform infrared (FTIR) measurement was performed on the lyophilized silk spheres prepared either from dissolving the silk/PVA blend films (casted from the silk/PVA blend solution of 2.5 wt % silk/2.5 wt % PVA, or from the silk/PVA blend solution of 1.0 wt % silk/4.0 wt % PVA) or from the methanol-treated silk/PVA blend solution. The different treatments of silk/PVA blend films were also evaluated, e.g., direct dissolution, water vapor-treatment (water-annealing), and film-stretching. The as-cast films were previously reported to exhibit initially a mostly amorphous structure (1538 cm$^{-1}$) with some silk I structure (1658 cm$^{-1}$, 1652 cm$^{-1}$). After water-annealing treatment, the silk I structure was predominant; and after methanol treatment the silk II structure (1697 cm$^{-1}$, 1627 cm$^{-1}$, 1528 cm$^{-1}$) largely increased with the formation of more than 50% of β-sheets. Jin et al., 2005. Once significant silk I structure (about 30% β-sheets) is formed, further methanol treatment is not able to convert it to silk II structure. Jin et al., 2005.

Silk spheres from the methanol-treated blend solution had approximately 50% β-sheet (silk II); whereas the silk spheres from different treatments of the blend films had about 30% β-sheet content (silk 1), as shown in Table 1:

TABLE 1

β-sheet content in the silk spheres prepared from the Silk/PVA blend film

| Sample | Silk/ PVA wt % | Treatment | β-sheet content (%) |
|---|---|---|---|
|  | 1.0/4.0 | Control: Silk/PVA Blend film prior to dissolution | 19 |
| 1 | 1.0/4.0 | Dissolving the film in water | 30 |
| 2 | 1.0/4.0 | Stretching, dissolving the film in water | 28 |
| 3 | 1.0/4.0 | Stretching, dissolving the film in 50% MeOH | 40 |
| 4 | 1.0/4.0 | Water annealing the film | 30 |
| 5 | 1.0/4.0 | 20% amplitude sonication | 42 |
| 6 | 1.0/4.0 | 50% MeOH added to blend solution | 48 |
|  | 2.5/2.5 | Control: Silk/PVA Blend film prior to dissolution | 27 |
| 7 | 2.5/2.5 | Dissolving the film in water | 28 |
| 8 | 2.5/2.5 | Stretching, dissolving the film in water | 30 |
| 9 | 2.5/2.5 | Stretching, dissolving the film in 50% MeOH | 32 |
| 10 | 2.5/2.5 | Water annealing the film | 33 |

Similar to the role of water vapor on silk films, PVA also promoted the formation of silk I structure in the dried silk spheres, perhaps due to hydrogen bonding formation between hydroxyl groups of PVA and silk. Furthermore, when the silk spheres with silk I structure were treated with 50% (v/v) methanol for 24 hours, the β-sheet content in the silk/PVA blend film casted from the silk/PVA blend solution with 1.0 wt % silk/4.0 wt % PVA increased to about 40%, while the β-sheet content in the blend film casted from the silk/PVA blend solution with 2.5 wt % silk/2.5 wt % PVA did not increase. One possible reason is that PVA molecules distributed randomly in silk spheres and might have induced the spatial proximity of silk molecules, and thus promoted silk structural transition from random coils to β-sheets. The intermolecular interaction between silk and PVA in the blend film cast from the 1.0 wt % silk/4.0 wt % PVA blend solution was higher compared to that in the blend film casted from the 2.5 wt % silk/2.5 wt % PVA; hence the silk structural transition in the silk/PVA blend film cast from the 1.0 wt % silk/4.0 wt % PVA blend solution proceeded further towards silk II under the methanol treatment. In addition, silk films with water-annealing treatment lost their weights much faster than those with methanol treatment, when the films with these treatments were incubated in a protease solution. Jin et al., 2005. Therefore, the silk spheres prepared from the silk:PVA blend films possess faster in vitro and in vivo degradation rates than those prepared by the methanol treatment (Hofmann et al., 2006; Wang et al., 2007), thus providing alternative options for materials used as drug deliveries carriers, where different degradation rates of the material are needed.

Figure 2:
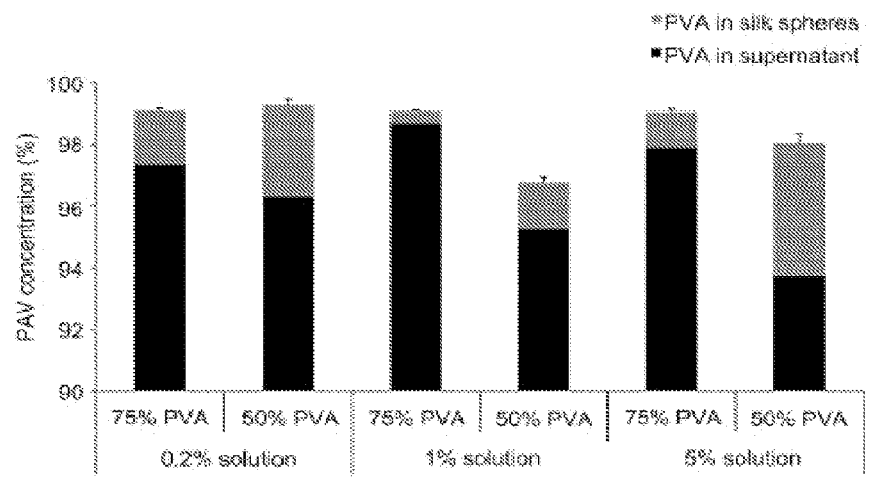
FIG. 2 depicts the profile of the residual PVA concentration determined in the supernatant fractions after the preparation of silk spheres (black columns) and in the silk spheres after the protease XIV digestion (gray columns). Data are shown as mean±S.D. (n=3-4).

According to the present embodiments, at least a portion of the PVA is removed after the silk/PVA blend films are dissolved in water to form silk spheres. PVA may be removed through any technique known in the art. For example, centrifugation may be used and the supernatant containing PVA removed. In one embodiment, to determine the residual PVA content in silk spheres, the spheres were prepared from the silk/PVA blend films and washed once with water. The PVA content in both silk spheres and the supernatant fractions after centrifugation was determined. Protease XIV is an efficient enzyme to digest silk materials. Horan et al., 26 Biomats. 3385-93 (2005). By using Protease XIV, silk spheres were digested and the residual PVA were released. As shown in FIG. 2, less than 5 wt % PVA remained in all silk spheres tested. The result was also confirmed by the PVA content determined in the supernatants. Because PVA is a FDA-approved ingredient used widely in oral and intraocular drug formulation, a small amount of residual PVA in silk spheres will not limit the biomedical applications of silk spheres.

According to the embodiments of the present invention, silk microparticles and nanoparticles with variant shapes may be obtained. Changing the shape of silk particles may be desirable in applications, such as using silk particles for drug delivery, because the sphere shape may affect the in vivo degradation and drug release behaviors of the spheres, as suggested in the literature. Rytting et al., 2008. As used herein, the term "silk spheres" include silk particles in a round, spherical shape, as well as silk particles in other shapes that deviate from the spherical shape, such as a spindle-shape or a disk-shape. The shape of the silk nanospheres and microspheres of the present invention may be controlled by applying different constraints on the silk/PVA blend film before dissolving the film in water. For example, water vapor (water-annealing) treatment of the silk/blend film may result the silk spheres in a flattened disk shape. The applied constraints on the silk/PVA blend film may also be physical forces, such as stretching forces, which can irreversibly change the shape of silk spheres in the blend films. For example, the silk/PVA blend films can be stretched before being dissolved in water. The resulting silk spheres, especially those with a size in micrometers, were elongated and spindle-shaped instead of spherical (FIGS. 1H, 1I). Some spheres were damaged during stretching and their interior porous structure was exposed (FIG. 1H inset). The spindle-shaped particles retained their shape when the stretched blend films were treated with either 50% (v/v) methanol or water vapor prior to dissolving in water. The stretching force converts the silk microspheres or nanospheres into spindle-shaped microparticles or spindle-shaped nanoparticles. Uniform silk microparticles or nanoparticles (such as spindle-shaped particles or flattened disk-shaped particles) may be obtained by adjusting the particle size and size distribution of silk microspheres or nanospheres in the blend film before applying constraints. Other physical forces, such as compressing and twisting, can also generate silk spheres with different shapes.

During the phase separation of silk and PVA, while mixing the two solutions, strong hydrogen bonds form between silk and PVA, thus quickly converting silk random coil structure to the stable silk I. Thus, silk phase separation in PVA solution can be manipulated to reduce the hydrogen bond formation between silk and PVA, or one may apply higher energy (e.g., ultrasonication) to the blend solution to disrupt possible large silk macro- or microphases.

The particle sizes and size distribution of silk spheres of the present invention may be controlled by adjusting one or more parameters during the fabrication process, such as the weight ratio of silk fibroin and PVA in the silk/PVA blend solution, the concentrations of silk fibroin and PVA in the silk/PVA blend solution, the molecular weight of PVA, or applying ultrasonification to the silk/PVA blend solution before drying the solution to form a film.

The size distribution of silk spheres of the present invention may be characterized by Polydispersity index (PDI). PDI of silk spheres size distribution is determined by methods commonly known by one of ordinary skill in the art, for example, by dynamic light scattering (DLS) measurement. With regard to DLS used for particle size determinations, the common use of second or third order cumulant analyses to fit the autocorrelation function leads to the values of PDI. The absolute value of PDI determined from this method ranges from zero and higher, with small values indicating narrower distributions. For example, PDI ranging from 0 to about 0.3 or from 0 to about 0.4 presents relatively monodisperse particle size distributions. This criterion has been generally accepted in the art of dynamic light scattering for particle size determinations.

The concentrations of silk fibroin and PVA in the silk/PVA blend solution may be adjusted to narrow the size distribution and to obtain homogeneous silk micro- or nanospheres. The weight ratio of silk and PVA in the blend solution is the factor to determine the phase separation. The concentrations of silk fibroin and PVA in the blend solution also affect the interaction between silk and PVA. The concentrations of silk fibroin and PVA in the blend solution can be as low as 0.02 wt % and as high as 15 wt %, if solubility of silk fibroin and PVA permits. The concentrations and weight ratio of silk fibroin and PVA in the silk/PVA blend solution can be adjusted easily, for example, by choosing concentrations of silk and PVA starting solutions and the volumes of silk and PVA starting solutions that are blended. The concentrations of silk fibroin and PVA starting solutions may be the same or different. In one embodiment, the purified silk aqueous solution is about 8 wt %, which can be diluted almost infinitely or concentrated up to 30 wt %. The highest concentration of PVA achievable is affected by the molecular weight of PVA. For example, when PVA with a molecular weight of 30,000-70,000 is used, a concentration of PVA higher than 8 wt % may not be easily achieved due to the solubility of PVA in water.

One approach to adjusting the weight ratio of silk and PVA in the blend solution is to keep the concentrations of silk starting solution and PVA starting solution the same, while adjusting the volumes of the starting solutions to be mixed. In certain embodiments of the present invention, silk and PVA starting solutions with equal concentrations of 0.02 wt %, 0.2 wt %, 1 wt % or 5 wt %, were used. The concentrations of both silk starting solution and PVA starting solution used for preparation of silk/PVA blend solution could be as high as 30 wt %. Exemplary final concentrations of silk and PVA in the blend solution are shown in Table 2:

TABLE 2

Concentrations in the silk/PVA blend solution

| Concentrations of silk and PVA in starting solutions | Concentrations of silk and PVA in blend solution, ratio of silk/PVA 1/1 | Concentrations of silk and PVA in blend solution, ratio of silk/PVA 1/4 |
| --- | --- | --- |
| 30 wt % (silk) | 15 wt % (silk) | 6 wt % (silk) |
| 30 wt % (PVA) | 15 wt % (PVA) | 24 wt % (PVA) |
| 8 wt % (silk) | 4 wt % (silk) | 1.6 wt % (silk) |
| 8 wt % (PVA) | 4 wt % (PVA) | 6.4 wt % (PVA) |
| 5 wt % (silk) | 2.5 wt % (silk) | 1.0 wt % (silk) |
| 5 wt % (PVA) | 2.5 wt % (PVA) | 4.0 wt % (PVA) |
| 1 wt % (silk) | 0.5 wt % (silk) | 0.2 wt % (silk) |
| 1 wt % (PVA) | 0.5 wt % (PVA) | 0.8 wt % (PVA) |
| 0.2 wt % (silk) | 0.1 wt % (silk) | 0.04 wt % (silk) |
| 0.2 wt % (PVA) | 0.1 wt % (PVA) | 0.16 wt % (PVA) |
| 0.02 wt % (silk) | 0.01 wt % (silk) | 0.004 wt % (silk) |
| 0.02 wt % (PVA) | 0.01 wt % (PVA) | 0.016 wt % (PVA) |

Figure 3:
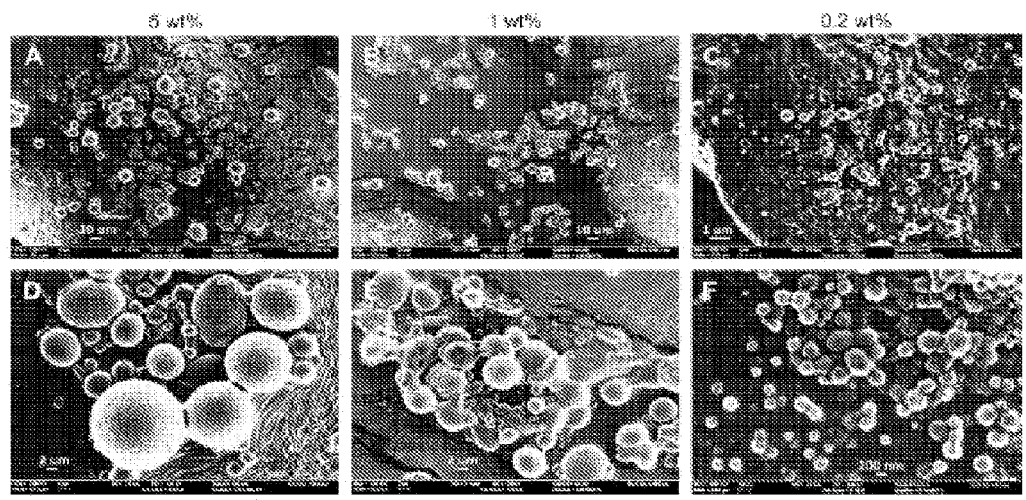
FIGS. 3A-3F are a series of scanning electron microscopic images of silk spheres, where the size of the sphere is controlled by adjusting the concentrations of silk and PVA in the silk/PVA blend solution.

To reduce the interaction of silk with PVA, the weight ratio between silk and PVA in the blend solution was adjusted to 1:4, and the concentrations of silk starting solution and PVA starting solution used for mixing were decreased from 5 wt % to either 1 wt % or 0.2 wt %. In other words, the concentration of silk in the blend solution was decreased from 1 wt % to either 0.2 wt % or 0.04 wt %; and the concentrations of PVA in the blend solution was decreased from 4 wt % to either 0.8 wt % or 0.16 wt %, accordingly. Characterized by SEM, silk spheres prepared from the 1 wt % silk/4 wt % PVA blend solution had a broad size distribution from nanometers to micrometers; no significant improvement was observed for silk spheres prepared from the 0.2 wt % silk/0.8 wt % PVA blend solution; but silk spheres prepared from 0.04 wt % silk/0.16 wt % PVA blend solution were dominated by nanospheres with a relatively homogeneous sizes distribution (100 nm-500 nm) (FIG. 3).

Figure 4:
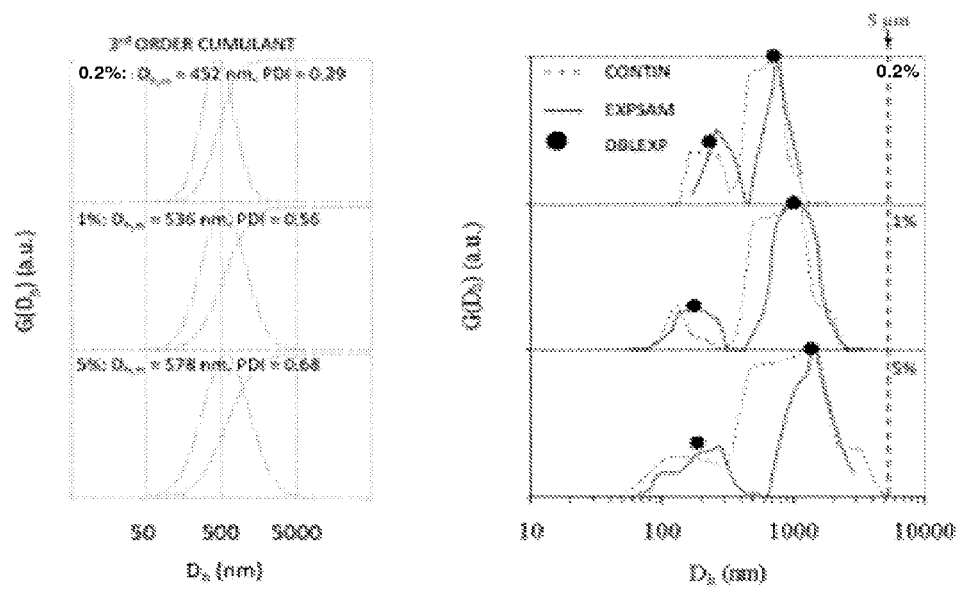
FIG. 4 depicts the dynamic light scattering measurement of silk spheres, where the size of the spheres was controlled by adjusting the concentrations of silk and PVA in the silk/PVA blend solution. The concentrations of silk and PVA starting solutions used for blending at ratios of 1:4 silk:PVA were 0.2 wt %, 1 wt % and 5 wt %. The final concentrations of silk/PVA in the blend solution were 0.04% silk/0.16% PVA, 0.2% silk/0.8% PVA, and 1.0% silk/4.0% PVA, respectively. The samples (water suspension of silk spheres) were filtered with a 5 µm membrane prior to the measurement.

The silk spheres were also subjected to dynamic light scattering measurement. For this characterization, silk spheres suspension in water was filtered through a 5 μm membrane by Millex®-SV (Millipore, Billerica, Mass.) before being measured. The silk spheres made from the 0.04 wt % silk/0.16 wt % PVA blend solution showed a relatively homogeneous size distribution with the mean sphere size of 452 nm, a polydispersity index (PDI) of PDI 0.29, and no spheres lager than 2 μm (FIG. 4). The silk spheres made from the 0.2 wt % silk/0.8 wt % PVA blend solution and silk spheres made from the 1 wt % silk/4 wt % PVA blend solution, however, had larger mean sizes (536 nm and 578 nm, respectively) and PDIs (PDI 0.56 and PDI 0.68, respectively), and a sphere size range from 100 nm to 5 μm (FIG. 4). The result was consistent with that observed by SEM. Without being bound by theory, it appears that because the formation of hydrogen bonding between silk and PVA hydroxyl groups stabilizes the silk sphere structure, lower polymer concentrations can alter the interaction and thus control both the sphere size and the size distribution.

Increasing the PVA content in blend solution does not, apparently, change size distribution. Hence, the weight ratio (or mass concentration ratio) of PVA in the blend solution can be higher than 4-times the silk concentration in the blend solution. Theoretically, the concentration of PVA in the blend solution can be infinitely high. A higher PVA concentration in the blend solution, however, is limited by the solubility of PVA in water. For example, when PVA having an average molecular weight of 30000-70000 is used, the concentration of PVA in solution may not reach higher than 8 wt %. In addition, when the weight ratio (or mass concentration ratio) of PVA in the blend solution is higher than 4-times the silk concentration in the blend solution, the isolation process of silk spheres from the aqueous phase can be less efficient than that of blend solution having a higher weight ratio of silk/PVA.

Decreasing the concentration of silk in blend solutions reduces the size and the size distribution of silk spheres. In particular, silk nanospheres with relative homogeneous size distribution may be prepared by decreasing the silk concentration in the silk/PVA blend solution. For example, silk spheres prepared from a 0.04 wt % silk/0.16 wt % PVA blend solution were dominated by silk nanospheres with a relatively homogeneous sizes distribution. In principle, silk and PVA solutions may be diluted almost infinitely to prepare silk spheres with smaller size and size distribution. Drying the diluted blend solutions, however, would require longer time and larger containers.

Using PVA with different molecular weights may also impact sphere size and size distribution. Tanaka et al., 1998. The molecular weight of PVA may also impact the solubility of the silk/PVA films, hence affecting the preparation of silk spheres. The average molecular weight of PVA used in the present embodiments may be generally within the range of 30,000-124,000. In one embodiment of the present invention, PVA has an average molecular weight of 30,000-70,000. In another embodiment, PVA has an average molecular weight of 85,000-124,000. When PVA with a higher molecular weight is employed, a longer incubation time (i.e., several hours) may be needed to dissolve the silk/PVA blend films. When the molecular weight of PVA reaches a certain limit (e.g., MW=146,000-186,000), however, the silk/PVA blend films were insoluble in water, even after lengthy (several days) incubation at either room temperature or at 60° C. These results suggested that the hydrogen bonds formed between the silk and PVA may be too strong to be broken by hydration when using high molecular weight PVA.

Figure 5:
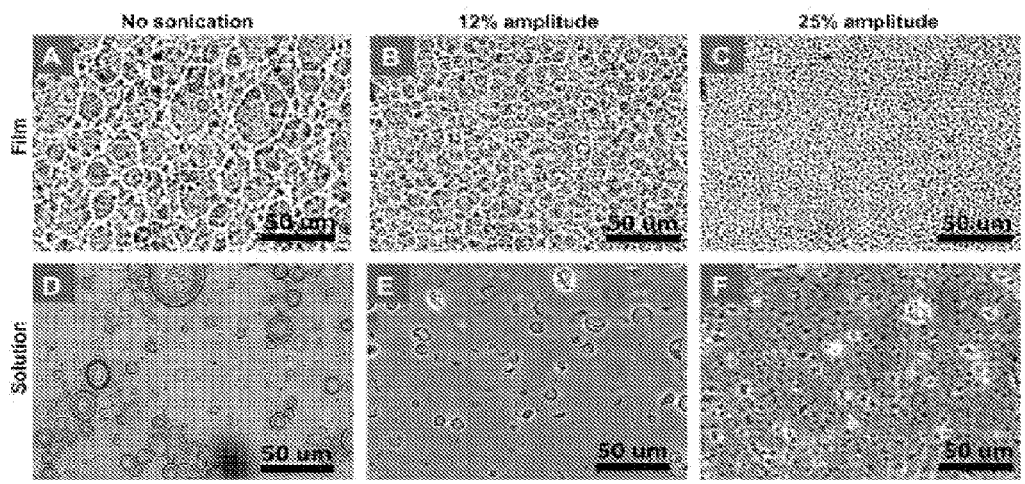
FIGS. 5A-5F are micrographs of silk spheres in which the size of the spheres was controlled by applying ultrasonication on the silk/PVA blend solution prior to casting the solution into film. The silk/PVA blend solution contained 1.0% silk/4.0% PVA (wt %). Control samples (no sonication) contained silk spheres with a broad distribution of sizes, ranging from nanometers to micrometers in both the blend film (FIG. 5A) and the water suspension (FIG. 5D). The sample sonicated with 12% energy output was dominated by microspheres ranging from 5 µm to 10 µm in both the blend film (FIG. 5B) and the water suspension (FIG. 5E). The sample sonicated with 25% energy output was dominated by nanospheres in both the blend film (FIG. 5C) and the water suspension (FIG. 5F). Scale bar is 50 µm.

The size and size distribution of the silk spheres of the present invention may also be adjusted by applying forces, such as by applying ultrasonification, on the silk/PVA blend solution before drying the solution into film. In this regard, the energy output of sonication may be further varied to affect the silk/PVA phase separation. In particular, silk nanospheres with relative homogeneous size distribution may be prepared by applying sonication with high energy output to the silk/PVA blend solution. The energy output of sonication used may depend on the volume of solution to be sonicated. The energy output of sonication should be sufficiently high so as to break down bigger spheres. For example, for a blend solution with a volume of 5 ml, 12% sonication energy output (corresponding to 4 watts) may break bigger spheres into micrometer size; and 25% sonication energy output (corresponding to 8 watts) may be high enough to break most spheres down to a nanometer size. In one embodiment, for example, 1 wt % silk/4 wt % PVA blend solutions were used to prepare silk spheres. When 12% and 25% of sonication energy output were used for a blend solution with a volume of 5 ml, the casted silk/PVA blend films were dominated by microspheres and nanospheres, respectively, characterized by a light microscope (FIG. 5). The energy output with 12% amplitude could disrupt some bigger spheres, resulting in smaller silk microspheres with a size range of 5 µm to 10 µm. The 25% sonication energy output, however, was high enough to yield primarily spheres of nanometer size. The results were confirmed by the dynamic light scattering (DLS) measurement. The 25% sonication energy output treated silk spheres were filtered through a 5 µm membrane and subjected to the DSL measurement. Such treated silk spheres had a mean sphere size of 322 nm, PDI 0.4, with no spheres larger than 2 µm. The 12% sonication energy output treated silk spheres also contained a portion of nanospheres with similar sizes as that of the 25% sonication energy output treated silk spheres. The concentration of these nanospheres, however, were approximately four times lower than that of the 25% sonication energy output treated silk spheres, as estimated by comparing the light scattering intensities of the two samples. Therefore, changing sonication energy output, i.e., energy input in the blend solution, directly affects the size and size distribution of silk spheres covering both micro- and nanometer ranges. Further, the β-sheet content in the silk spheres prepared by the 25% amplitude sonication was determined by FTIR, and showed a significant increase (approximately 12%) as compared to the silk spheres without the sonication treatment, indicating the formation of crystal silk II structure (Table 1).

In the present invention, the continuous PVA phase in the blend film functions to freeze and lock the size and shape of silk spheres embedded in it; and it also induces formation of β-sheet structure. Hence, methods that may influence the silk and PVA phase separation in the blend solution, while not disturbing silk β-sheet structure formation, may be used to control the sphere size and size distribution of silk spheres. For example, supplementation of silk/PVA blend solution with 3 wt % to 8 wt % glycerin may reduce phase separation in the blend films, perhaps because the interaction between PVA and silk is influenced by the hydroxyl groups in glycerin. Dai et al., 86 J. Appl. Polym. Sci. 2342-47 (2002). Hence, adding glycerin or other hydroxyl group-rich compounds or polymers to a blend silk/PVA solution may be used as an alternative to lowering polymer concentration for the preparation of silk nanospheres. Other factors, such as salt concentration, pH, etc., may also influence the phase separation. Thus the silk size and size distribution may be controlled by one or more of the following: (a) adding glycerin or other hydroxyl group-rich compounds or polymers to silk/PVA blend solution; (b) adjusting pH of silk/PVA blend solution; or (c) adding salt to a silk/PVA blend solution and, optionally, adjusting salt concentration of silk/PVA blend solution. Some additional factor that may be adjusted to narrow the size distribution include controlling the drying speed (a few minutes up to 3 days) and incubating temperature (4° C. up to 60° C.), but no obvious change of sphere size distribution was observed under the microscope for these factors. Perhaps these treatments do not induce silk microphase agglomeration or dispersion.

The methods of the present invention may further comprise removing the silk microspheres from the silk nanospheres, or removing the nanospheres from the microspheres depending on the applications. The spheres with undesirable sizes can be removed easily by separation techniques, known by one skilled in the art, such as filtration or centrifugation. For example, in one embodiment described herein, silk nanospheres with the mean sphere size of less than 500 nm and no spheres larger than 2 µm were prepared. Silk nano spheres can be filtrated with a 500 nm membrane that removes spheres larger than 500 nm.

Further, the present invention provides for silk fibroin microspheres compositions or silk fibroin nanospheres prepared by any of the methods of the present invention described in the above embodiments herein.

The embodiments of the present invention also provides for methods of encapsulating an active agent, such as a bioactive agent or chemicals, in porous silk spheres with the size of the spheres ranging from nanometers to micrometers, comprising the steps of (a) mixing an aqueous silk fibroin solution and an active agent with an aqueous PVA solution; (b) drying the solution of step (a) to form a film; (c) dissolving the film of step (b) in water; and (d) removing at least a portion of the PVA, thereby forming the active agent encapsulated silk spheres. The present invention also encompasses the active agent encapsulated silk spheres compositions resulting from the methods described herein.

Silk fibroin solution may be mixed with one or more active agents. The active agent may be any agent known by those of skill in the art to have bioactivity or chemical activity, such as a therapeutic agent or a biological material. Suitable active agents include, but not limited to, chemicals, cells (including stem cells), proteins, peptides, nucleic acids (e.g., DNA, RNA, siRNA), nucleic acid analogues, nucleotides, oligonucleotides or sequences, peptide nucleic acids (PNA), aptamers, antibodies or fragments or portions thereof (e.g., paratopes or complementarity-determining regions), antigens or epitopes, hormones, hormone antagonists, cell attachment mediators (such as RGD), growth factors or recombinant growth factors and fragments and variants thereof, cytokines, enzymes, antioxidants, antibiotics or antimicrobial compounds, anti-inflammation agents, antifungals, viruses, antivirals, toxins, prodrugs, drugs, dyes, amino acids, vitamins, chemotherapeutic agents, small molecules, and combinations thereof. The agent may also be a combination of any of the above-mentioned active agents. Encapsulating either a therapeutic agent or biological material, or the combination of them, is desirous because the encapsulated product can be used for numerous biomedical purposes.

Exemplary bioactive agents include bone morphogenetic proteins (e.g., BMPs 1-7), bone morphogenetic-like proteins (e.g., GFD-5, GFD-7, and GFD-8), epidermal growth factor (EGF), fibroblast growth factor (e.g., FGF 1-9), platelet derived growth factor (PDGF), insulin like growth factors (IGF-I and IGF-II), transforming growth factors (e.g., TGF-α, TGF-βI-III), erythropoietin (EPO), YIGSR peptides, glycosaminoglycans (GAGs), hyaluronic acid (HA), integrins, selectins, and cadherins, vascular endothelial growth factor (VEGF); analgesics and analgesic combinations; steroids; antibiotics; insulin; interferons α and y; interleukins; adenosine; chemotherapeutic agents (e.g., anticancer agents); tumor necrosis factors α and β; antibodies; cell attachment mediators, such as RGD or integrins, or other naturally derived or genetically engineered proteins, polysaccharides, glycoproteins, cytotoxins, prodrugs, immunogens, or lipoproteins. Growth factors are known in the art, see, e.g., Rosen & Thies, Cellular & Mol. Basis Bone Formation & Repair (R.G. Landes Co.).

In some embodiments, the active agent may also be an organism such as a fungus, plant, animal, bacterium, or a virus (including bacteriophage). Moreover, the active agent may include neurotransmitters, hormones, intracellular signal transduction agents, pharmaceutically active agents, toxic agents, agricultural chemicals, chemical toxins, biological toxins, microbes, and animal cells such as neurons, liver cells, and immune system cells. The active agents may also include therapeutic compounds, such as pharmacological materials, vitamins, sedatives, hypnotics, prostaglandins and radiopharmaceuticals.

Exemplary cells suitable for use herein may include, but are not limited to, progenitor cells or stem cells, smooth muscle cells, skeletal muscle cells, cardiac muscle cells, epithelial cells, endothelial cells, urothelial cells, fibroblasts, myoblasts, oscular cells, chondrocytes, chondroblasts, osteoblasts, osteoclasts, keratinocytes, kidney tubular cells, kidney basement membrane cells, integumentary cells, bone marrow cells, hepatocytes, bile duct cells, pancreatic islet cells, thyroid, parathyroid, adrenal, hypothalamic, pituitary, ovarian, testicular, salivary gland cells, adipocytes, and precursor cells. The active agents can also be the combinations of any of the cells listed above. See also WO 2008/106485; PCT/US2009/059547; WO 2007/103442.

Exemplary antibodies that may be incorporated in silk spheres include, but are not limited to, abciximab, adalimumab, alemtuzumab, basiliximab, bevacizumab, cetuximab, certolizumab pegol, daclizumab, eculizumab, efalizumab, gemtuzumab, ibritumomab tiuxetan, infliximab, muromonab-CD3, natalizumab, ofatumumab omalizumab, palivizumab, panitumumab, ranibizumab, rituximab, tositumomab, trastuzumab, altumomab pentetate, arcitumomab, atlizumab, bectumomab, belimumab, besilesomab, biciromab, canakinumab, capromab pendetide, catumaxomab, denosumab, edrecolomab, efungumab, ertumaxomab, etaracizumab, fanolesomab, fontolizumab, gemtuzumab ozogamicin, golimumab, igovomab, imciromab, labetuzumab, mepolizumab, motavizumab, nimotuzumab, nofetumomab merpentan, oregovomab, pemtumomab, pertuzumab, rovelizumab, ruplizumab, sulesomab, tacatuzumab tetraxetan, tefibazumab, tocilizumab, ustekinumab, visilizumab, votumumab, zalutumumab, and zanolimumab. The active agents can also be the combinations of any of the antibodies listed above.

Exemplary antibiotic agents include, but are not limited to, actinomycin; aminoglycosides (e.g., neomycin, gentamicin, tobramycin); β-lactamase inhibitors (e.g., clavulanic acid, sulbactam); glycopeptides (e.g., vancomycin, teicoplanin, polymixin); ansamycins; bacitracin; carbacephem; carbapenems; cephalosporins (e.g., cefazolin, cefaclor, cefditoren, ceftobiprole, cefuroxime, cefotaxime, cefipeme, cefadroxil, cefoxitin, cefprozil, cefdinir); gramicidin; isoniazid; linezolid; macrolides (e.g., erythromycin, clarithromycin, azithromycin); mupirocin; penicillins (e.g., amoxicillin, ampicillin, cloxacillin, dicloxacillin, flucloxacillin, oxacillin, piperacillin); oxolinic acid; polypeptides (e.g., bacitracin, polymyxin B); quinolones (e.g., ciprofloxacin, nalidixic acid, enoxacin, gatifloxacin, levaquin, ofloxacin, etc.); sulfonamides (e.g., sulfasalazine, trimethoprim, trimethoprim-sulfamethoxazole (co-trimoxazole), sulfadiazine); tetracyclines (e.g., doxycyline, minocycline, tetracycline, etc.); monobactams such as aztreonam; chloramphenicol; lincomycin; clindamycin; ethambutol; mupirocin; metronidazole; pefloxacin; pyrazinamide; thiamphenicol; rifampicin; thiamphenicl; dapsone; clofazimine; quinupristin; metronidazole; linezolid; isoniazid; piracil; novobiocin; trimethoprim; fosfomycin; fusidic acid; or other topical antibiotics. Optionally, the antibiotic agents may also be antimicrobial peptides such as defensins, magainin and nisin; or lytic bacteriophage. The antibiotic agents can also be the combinations of any of the agents listed above. See also PCT/US2010/026190.

Exemplary enzymes suitable for use herein include, but are not limited to, peroxidase, lipase, amylose, organophosphate dehydrogenase, ligases, restriction endonucleases, ribonucleases, DNA polymerases, glucose oxidase, laccase, and the like. Interactions between components may also be used to functionalize silk fibroin through, for example, specific interaction between avidin and biotin. The active agents can also be the combinations of any of the enzymes listed above. See PCT/US2010/042585.

When introducing therapeutic agents or biological material into the silk fibroin, other materials known in the art may also be added with the agent. For instance, it may be desirable to add materials to promote the growth of the agent (for biological materials), promote the functionality of the agent after it is released from the silk mats, or increase the agent's ability to survive or retain its efficacy during the period it is embedded in the silk. Materials known to promote cell growth include cell growth media, such as Dulbecco's Modified Eagle Medium (DMEM), fetal bovine serum (FBS), non-essential amino acids and antibiotics, and growth and morphogenic factors such as fibroblast growth factor (FGF), transforming growth factors (TGFs), vascular endothelial growth factor (VEGF), epidermal growth factor (EGF), insulin-like growth factor (IGF-I), bone morphogenetic growth factors (BMPs), nerve growth factors, and related proteins may be used.

Additional options for delivery via the silk spheres include DNA, siRNA, antisense, plasmids, liposomes and related systems for delivery of genetic materials; peptides and proteins to activate cellular signaling cascades; peptides and proteins to promote mineralization or related events from cells; adhesion peptides and proteins to improve silk mats-tissue interfaces; antimicrobial peptides; and proteins and related compounds.

The silk spheres with embedded active agents or biological materials may be suitable for long term storage and stabilization of the cells and/or active agents. Cells and/or active agents, when incorporated in the silk spheres, can be stable (i.e., maintaining at least 50% of residual activity) for at least 30 days at room temperature (i.e., 22° C. to 25° C.) and body temperature (37° C.). Hence, temperature-sensitive active agents, such as some antibiotics, can be stored in silk mats without refrigeration. Importantly, temperature-sensitive bioactive agents can be delivered (e.g., through injection) into the body in silk spheres and maintain activity for a longer period of time than previously imagined.

The silk-fibroin embedded active agents (e.g., therapeutic agents) or biological materials are suitable for a biodelivery device.

Silk spheres may also be combined with other silk fibroin materials as a silk composite material as a biodelivery device. For example, to embed silk spheres of the present invention into silk mats, silk films, silk fiber, silk hydrogel, silk sponges, silk meshes, silk 3-D scaffold, etc. Other silk fibroin materials used as biodelivery device may be found, for example, in U.S. patent application Ser. Nos. 10/541,182; 11/628,930; 11/664,234; 11/407,373; PCT/US07/020,789; PCT/US08/55072; PCT/US09/44117.

Some embodiments of the present invention relate to the utility of silk-fibroin embedded therapeutic agents or biological materials as biodelivery or drug delivery systems for potential utility in medical implants, tissue repairs and for medical device coatings.

The active agent, when mixed with the silk fibroin solution, can be encapsulated in the silk spheres. The encapsulated bioactive agent can then be released from the silk spheres through typical release mechanisms known in the art. Maintaining the bioactive agent in an active form throughout the silk sphere preparation process enables it to be active upon release from the microsphere.

A pharmaceutical formulation may be prepared that contains the silk fibroin microspheres or nanospheres having encapsulated bioactive agents. The formulation can be administered to a patient in need of the particular bioactive agent that has been encapsulated in the microspheres.

The pharmaceutical formulation may be administered by a variety of routes known in the art including topical, oral, ocular, nasal, transdermal or parenteral (including intravenous, intraperitoneal, intramuscular and subcutaneous injection as well as intranasal or inhalation administration) and implantation. The delivery may be systemic, regional, or local. Additionally, the delivery may be intrathecal, e.g., for CNS delivery.

In addition to the silk spheres, the pharmaceutical formulation may also contain a targeting ligand. Targeting ligand refers to any material or substance which may promote targeting of the pharmaceutical formulation to tissues and/or receptors in vivo and/or in vitro with the formulations of the present invention. The targeting ligand may be synthetic, semi-synthetic, or naturally-occurring. Materials or substances which may serve as targeting ligands include, for example, proteins, including antibodies, antibody fragments, hormones, hormone analogues, glycoproteins and lectins, peptides, polypeptides, amino acids, sugars, saccharides, including monosaccharides and polysaccharides, carbohydrates, vitamins, steroids, steroid analogs, hormones, cofactors, and genetic material, including nucleosides, nucleotides, nucleotide acid constructs, peptide nucleic acids (PNA), aptamers, and polynucleotides. Other targeting ligands in the present invention include cell adhesion molecules (CAM), among which are, for example, cytokines, integrins, cadherins, immunoglobulins and selectin.

The pharmaceutical formulations may also encompass precursor targeting ligands. A precursor to a targeting ligand refers to any material or substance which may be converted to a targeting ligand. Such conversion may involve, for example, anchoring a precursor to a targeting ligand. Exemplary targeting precursor moieties include maleimide groups, disulfide groups, such as ortho-pyridyl disulfide, vinyl sulfone groups, azide groups, and iodo acetyl groups.

The pharmaceutical formulations may contain common components found in other pharmaceutical formulations, such as known excipients. Exemplary excipients include diluents, solvents, buffers, or other liquid vehicle, solubilizers, dispersing or suspending agents, isotonic agents, viscosity controlling agents, binders, lubricants, surfactants, preservatives, stabilizers and the like, as suited to particular dosage form desired. The formulations may also include bulking agents, chelating agents, and antioxidants. Where parenteral formulations are used, the formulation may additionally or alternately include sugars, amino acids, or electrolytes.

Some examples of materials which can serve as pharmaceutically acceptable carriers include, but are not limited to, sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatine; talc; oils such as peanut oil, cottonseed oil; safflower oil, sesame oil; olive oil; corn oil and soybean oil; esters such as ethyl oleate and ethyl laurate; agar; non-toxic compatible lubricants such as sodium lauryl sulfate and magnesium stearate; polyols, for example, of a molecular weight less than about 70,000 kD, such as trehalose, mannitol, and polyethylene glycol. See, e.g., U.S. Pat. No. 5,589,167. Exemplary surfactants include nonionic surfactants, such as Tween surfactants, polysorbates, such as polysorbate 20 or 80, etc., and the poloxamers, such as poloxamer 184 or 188, Pluronic polyols, and other ethylene/polypropylene block polymers, etc. Suitable buffers include Tris, citrate, succinate, acetate, or histidine buffers. Suitable preservatives include phenol, benzyl alcohol, metacresol, methyl paraben, propyl paraben, benzalconium chloride, and benzethonium chloride. Other additives include carboxymethylcellulose, dextran, and gelatin. Suitable stabilizing agents include heparin, pentosan polysulfate and other heparinoids, and divalent cations such as magnesium and zinc. Coloring agents, releasing agents, coating agents, sweetening, flavoring and perfuming agents, preservatives and antioxidants can also be present in the composition, according to the judgment of the formulator.

The pharmaceutical formulations containing the silk spheres encapsulating therapeutic agent can be administered in a controlled-release manner so that portions of the therapeutic agent are released in the patient over a period of time. The therapeutic agent may release quickly or slowly. For instance, the pharmaceutical formulation can be administered so that less than about 5% of the therapeutic agent is released in the patient from the silk spheres over a period of one month. Alternatively, a larger portion of the therapeutic agent may be released initially, with a smaller portion retained in the silk spheres and released later. For example, the pharmaceutical formulation can be administered so that at least 5% of the therapeutic agent remains in the silk spheres 10 days after administration.

When administering the therapeutic agent in a controlled-release manner, the therapeutic agent remains active in the spheres so that it can perform its therapeutic function upon release. Generally, pharmaceutical formulation contains silk spheres where the activity of the therapeutic agent in the silk spheres remains at a significant quantity that can sustain therapeutic effects within a clinically relevant period of time, which can be a week, a month, or even a year.

The silk spheres structure enables the biodelivery vehicle comprising silk spheres to have a controlled-release property. Controlled release permits dosages to be administered over time, with controlled release kinetics. In some instances, delivery of the therapeutic agent or biological material is continuous to the site where treatment is needed, for example, over several weeks. Controlled release over time, for example, over several days or weeks, or longer, permits continuous delivery of the therapeutic agent or biological material to obtain preferred treatments. The controlled delivery vehicle is advantageous because it protects the therapeutic agent or biological material from degradation in vivo in body fluids and tissue, for example, by proteases. See, e.g., PCT/US09/44117.

Controlled release of the active agent permits active agent to be released sustainably over time, with controlled release kinetics. In some instances, the bioactive agent is delivered continuously to the site where treatment is needed, for example, over several weeks. Controlled release over time, for example, over several days or weeks, or longer, permits continuous delivery of the bioactive agent to obtain preferred treatments. The controlled delivery vehicle is advantageous because it protects the bioactive agent from degradation in vivo in body fluids and tissue, for example, by proteases.

Controlled release from the silk spheres compositions may be designed to occur over time, for example, for greater than about 12 hours or 24 hours. The time of release may be selected, for example, to occur over a time period of about 12 hours to 24 hours; about 12 hours to 42 hours; or, e.g., about 12 to 72 hours. In another embodiment, release may occur for example on the order of about 1 day to 15 days. The controlled release time may be selected based on the condition treated. For example, longer times may be more effective for wound healing, whereas shorter delivery times may be more useful for some cardiovascular applications.

Controlled release of the bioactive agent from the silk spheres compositions in vivo may occur, for example, in the amount of about 1 ng to 1 mg/day, for example, about 50 ng to 500 ng/day, or, in one embodiment, about 100 ng/day. Delivery systems comprising therapeutic agent and a carrier may be formulated that include, for example, 10 ng to 1 mg therapeutic agent, or about 1 µg to 500 µg, or, for example, about 10 µg to 100 µg, depending on the therapeutic application.

In one embodiment, tetramethylrhodamine-conjugated bovine serum albumin (TMR-BSA), tetramethylrhodamine-conjugated dextran (TMR-Dextran) and rhodamine B (RhB) were used as model drugs. The drugs were mixed with aqueous silk fibroin solution (1/100 weight ratio) prior to blending with PVA. Rhodamine moiety emits red fluorescence after being excited. Thus, the distribution of the conjugated drug molecules in silk microspheres can be monitored and the drug loading and release can be readily determined. These model drugs have various molecular weights (TMR-BSA: 66,000; TMR Dextran: 10,000; RhB: 479 Da, respectively) and hydrophobicities (RhB>TMR-BSA>TMR-Dextran), and surface charge (RhB: positive, TMR-BSA: negative, TMR-Dextran: neutral), leading to distinguished features in the drug distribution, loading and release profiles.

Figure 6:
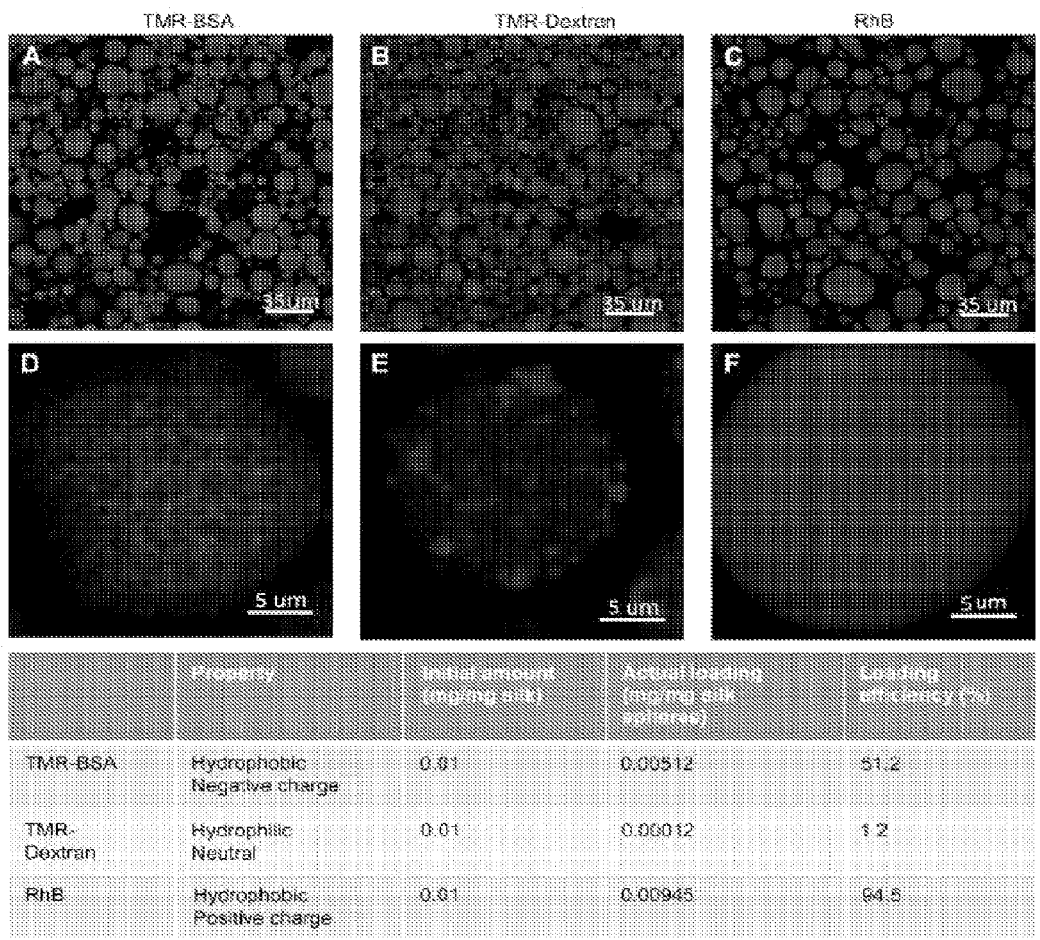
FIGS. 6A-6F depict the loading and distribution of model drugs in the silk spheres. The silk/PVA blend solution contained 1.0% silk/4.0% PVA (wt %). Tetramethylrhodamine conjugated bovine serum albumin (TMR-BSA), tetramethylrhodamine conjugated dextran (TMR-Dextran) or rhodamine B (RhB), were pre-mixed with silk fibroin solution before blending with PVA.

Characterized by the confocal laser scanning microscopy, the TMR-BSA-loaded spheres showed a porous structure with pores separated by red fluorescent fibers, similar to the porous structure observed by SEM (compare to FIGS. 6A, 6D and 1C). The red fluorescent fibers were likely the silk fibers associated with TMR-BSA. The strong interaction between TMR-BSA and silk fibers prevented TMR-BSA from diffusing into surrounding medium during the preparation of silk spheres. The loading efficiency of TMR-BSA was determined to be about 51% (FIG. 6). TMR-dextran-loaded spheres showed a weak red fluorescent background decorated by some strong red fluorescent aggregates (FIGS. 6B, 6E). TMR-dextran seemed to exist either as single molecules or as aggregates, distributing evenly in silk spheres with no strong association with silk fibric structure. The loading efficiency of TMR-dextran was approximately 1.2%, much less than that of TMR-BSA. Most of TMR-dextran was washed away during the preparation of silk spheres, due to the weaker binding of dextran to the silk fibroin. Lower molecular weight of dextran (compared to BSA) may also have contributed to the low drug loading efficiency, because molecules diffuse faster from the spheres. RhB-loaded silk spheres emitted very strong red fluorescence and no structural details could be identified in this case (FIGS. 6C, 6F). The loading efficiency was approximately 95%. RhB has both hydrophobic and positively charged moieties, both of which may have contributed to the strong binding of RhB to silk fibroin via hydrophobic interaction and electrostatic interaction (to the hydrophilic regions of silk molecules that present negative charges), resulting a high loading efficiency and a slow release profile. The strong binding of RhB with silk perhaps due to a combination of strong electrostatic and hydrophobic interactions. The negative charge and reduced hydrophobic interactions between silk and BSA can possibly lead to lower binding than that of RhB, while the hydrophilic nature of the dextran molecule can lead its low binding affinity to silk.

Figure 7:
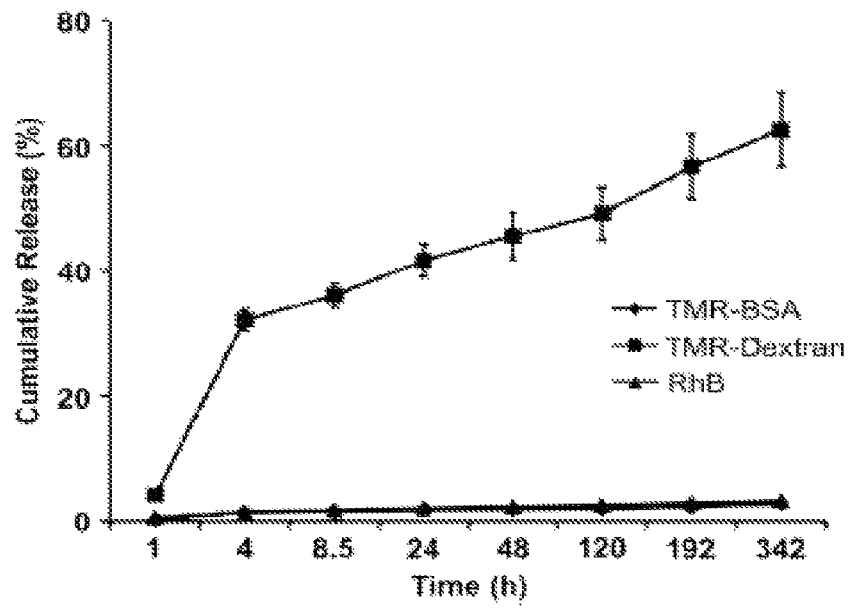
FIG. 7 depicts the cumulative drug release from silk spheres. Silk spheres loaded with model drugs were prepared from the silk/PVA blend films. The silk/PVA blend solution used to prepare the blend film contained 1.0% silk and 4.0% PVA (wt %). To determine the drug release profile, the silk spheres were centrifuged at certain desired time points and the drug concentrations in the supernatants measured.

The drug release profiles turned out to be a compromise between the silk-drug interaction and the molecular weight of the drug. Following a short and low-level (about 1%) initial burst release, perhaps due to the release of residual drug remained on or near the surface of silk spheres, the TMR-BSA and RhB were released slowly, with less than 5% of total loading being released within 2 weeks (FIG. 7). In contrast, TMR-dextran was released much faster, with more than 60% of total loading being released within two weeks at a nearly zero-order release rate (FIG. 7). Since the molecular weight of RhB is much lower than that of TMR-BSA and TMR-dextran, the results indicate that the interaction between silk and encapsulated drug, rather than the diffusion, might have controlled the drug release.

The amphiphilic nature of silk molecules facilitates the loading of both hydrophobic and hydrophilic drugs in silk spheres through intermolecular interactions between drugs and silk, in a similar manner as phospholipids. Hence controlling the drug loading and drug releasing rate of silk can be manipulating by controlling the degree of silk crystallinity (β-sheet formation) in the hydrophobic regions of silk and/or the charge states in the hydrophilic regions of silk. Because of the high molecular weight, amino acid composition and unique structure, silk vesicles are more chemically and physically stable and more suitable for delivering macromolecular drugs, compared to widely used lipid vesicles. Thus silk micro- and nanospheres compositions of the present invention are useful in a variety of applications concerning not only drug delivery but also tissue regeneration and enzyme catalysis.

Various formats of silk can be used as silk fibroin-based drug delivery systems, such as silk films, porous sponges, ultrathin coatings and nanofibers. Uebersax et al., 28 Biomats. 4449-60 (2007); Hofmann et al., 2006; Wang et al., 121 J Control Release 190-9 (2007); Bayraktar et al., 60 Eur J Pharm Biopharm 373-81 (2005); Wang et al., 29 Biomats. 894-903 (2008); Karageorgiou et al., 78 J Biomed Mater Res A. 324-34 (2006); Uebersax et al., 127 J Control Release 12-21 (2008); Li et al., 27 Biomats. 3115-2 (2006). These delivery systems were mainly studied for growth factors and cells for tissue engineering. The silk particles of the invention, based on the ability to control size and shape, can be incorporated in these systems and used as reservoir carriers for growth factors, providing a more sustained and controlled release. Spatial and temporal patterning of growth factors can also be achieved by incorporating silk nano-/microparticles in the systems.

Silk microspheres and nanospheres prepared with different other methods have also been reported. Wilz et al., 2008; Wang et al., 2007; Wang et al., 2009; Hino et al., 6 Pharm. Pharmacol. Commun 335-9 (2000); Wenk et al., 2008; Numata et al., 30 Biomats. 5775-84 (2009); Gupta et al., 4 Int J Nanomedicine 115-22 (2009); Zhang et al., 2007. Compared to these systems, the method of invention can control the size and shape of the particles according to specific requirements. The method requires no organic solvents and no expensive equipment during material processing; therefore, this is a green technology suitable for the future biomedical and pharmaceutical applications for drug delivery.

the drugs are encapsulated in the silk nanospheres, with activity of the drugs preserved, the drugs can be released in the target site with a controlled and sustained manner, avoiding the pre-degradation of the drugs before reaching the target site during blood circulation.

In particular, the present invention provides for a gene delivery (plasmid DNA delivery, small interfering RNA delivery) and drug delivery system to specific target tumors, tissues or cells for gene therapy. For example, the gene embedded silk nanospheres may be used as a nonviral gene vector. Silk nanospheres of the present invention ranges from one nanometer to one hundred nanometers to hundreds of nanometers, hence can penetrate small capillaries and cells, and pocess increase cellular uptake property. In addition, because silk nanospheres of the invention are biocompatible,

TABLE 3

Comparison of silk fibroin-based drug delivery systems

| Silk delivery system | Preparation | Dimension | Drug loaded | In vitro drug release |
|---|---|---|---|---|
| Microspheres | Lipid-template | 2-3 μm | Adenosine | 14 days |
| | | | HRP | >4 weeks |
| | | | BMP-2, IGF-I | >14 days |
| | PVA blend film | 5-10 μm | BSA | >4 weeks |
| | | | Dextran | 7 days |
| | | | Rhodamine B | >4 weeks |
| | Spray-drier | 5 μm | theophylline | N.D. |
| | Vibrational splitting of laminar jet | 101-440 μm | Salicylic acid | 1 day |
| | | | propranolol hydrochloride | 20 days |
| | | | IGF-I | >7 weeks |
| Nanospheres | PVA blend film | 300-400 nm | Same as silk/PVA microspheres | Same as silk/PVA microspheres |
| | Bioengineered silk | 300-400 nm | Plasmid DNA | N.D. |
| | capillary-microdot | <100 nm | Curcumin | >8 weeks |
| | Acetone mix/dialysis | 35-125 nm | L-asparaginase | N.D. |
| Film | Air-dry and Post-treatment | Micron thickness | NGF | >3 weeks |
| | | Micron thickness | Dextran, HRP, lysozyme | >4 weeks |
| Layer-by-layer coatings | Coat substrate | Submicron thickness | Rhodamine B, Azoalbumin | >2 weeks |
| | Coat drug tablet | N.D. | theophylline | >8 h |
| | Coat stents | 6 layers | Heperin | N.D. |
| Porous sponge | Drug absorbed | 300-400 mm pores | BMP-2 | >7 days |
| | Drug encapsulated | 200 300 mm pores | IGF-I | >4 weeks |
| Nano-fiber | Electro-spinning | Submicrondiameter | BMP-2 | N.D. |

Another embodiment of this invention relates to a drug delivery system comprising an active agent encapsulated in silk microspheres or nanospheres. The active agent may be a bioactive agent, such as one or more of the active agents discussed above.

One particular embodiment of the present invention relates to a drug-delivery system using silk nanospheres encapsulating bioactive agents. Such drug delivery system may be used to treat diseases such as brain disease. Because of the small sizes, silk nanospheres can diffuse quickly and circulate the bloodstream, and silk nanospheres can overcome numerous physiological barriers such as blood-brain barrier. For example, silk nanospheres encapsulating drugs can be injected into the bloodstream, safely cross the blood-brain barrier, and specifically target the brain-tumor cells. Because biodegradable, have low toxicity and can be targetable to specific cell types, they may serve as useful nonviral gene vector.

As defined herein, gene may refer to RNA, DNA, RNAi, siRNA, shRNAi, microRNAi, antisense oligonucleotides, RNA/DNA chimera, nucleic acid analogues such as PNA, pcPNA and LNA, natural and artificial nucleotides or sequences, or combinations of these, and the like, without limitation.

The gene delivery system may be administered through methods known in the art. Generally the delivery methods include, but not limited to, physical methods such as microinjection, gene gun, impalefection, hydrostatic pressure, electroporation, continuous infusion, and sonication and chemical, such as lipofection. It can also include the use of polymeric gene carriers (polyplexes).

To further enhance the introduction efficiency and its specificity of the gene delivery system to cells, specific peptide sequences tailored to certain disease, for example, cell binding motifs, cell penetrating peptides, signal peptides of virus, tumor-homing peptides, and metal binding domain for coating micro or nano magnetic particles to heat and kill disease cells, can be coated or conjugated to the surface of silk nanospheres.

The encapsulation process of the present invention does not have to be used in the field of pharmaceutical formulations and drug delivery methods. The silk fibroin micro- and nanocapsules may encapsulate various other active agents useful in a variety of fields. For instance, the active agent may be an enzyme or an enzyme-based electrode. The enzyme or enzyme-based electrode may be used in the field of tissue engineering, biosensors, the food industry, environmental control, or biomedical applications. The system can also be used as a reservoir for a variety of needs, such as in the food industry to harbor vitamins, nutrients, antioxidants and other additives; in the environmental field to harbor microorganisms for remediation or water treatments; in materials as additives to serve as a source of in situ detection and repair components, such as for nondestructive evaluation of material failures and self-repairs of the materials; and for biodetection schemes to help stabilize cells, molecules and related systems.

The silk microspheres and nanospheres compositions of the present invention may also be used as a storage-stable medium for active agents. Such storage-stable active agent-embedded silk medium may be prepared from entrapping the active agents in the water-insoluble silk spheres, with the silk spheres already separated from aqueous solution phase, for example a powder composition comprising silk spheres entrapping active agents. Alternatively, the active agents may also be stored in the silk/PVA blend solution or the dehydrated silk/PVA blend film. For storage purposes, the silk medium entrapping the active agents in this regard may or may not be further processed to silk spheres. Hence the present invention provides for silk fibroin, processed into film formats or silk spheres formats, which provides efficient and highly effective carrier for the long-term stabilization of entrapped active agents, as well as better control of activity and release.

The unique chemistry, structure, and assembly of silk fibroin protein offers a unique environment in which active agent can be stabilized and remain active over extended periods of time. Without the use of harsh chemical conditions and organic solvents, active agents can be entrapped easily in silk blend films, silk spheres, and their activity retained in the nano- and micro-environments formed during phase separation and silk structure transition. Silk fibroin is also thermodynamically stable once transition into beta-sheet structure. Hence these features provide a suitable stable silk matrix to stabilize active agents as described herein.

The active agents for long-term storage in the present invention may include any agents that have chemical activity or bioactivity. The agent of interest include, but not limited to, chemicals, naturally derived or genetically engineered proteins and peptides, nucleic acids, nucleic acid analogues, natural and artificial nucleotides, oligonucleotides or sequences, peptide nucleic acids, aptamers, antibodies, hormones, hormone antagonists, growth factors or recombinant growth factors and fragments and variants thereof, cytokines, enzymes, antibiotics, viruses, antivirals, toxins, prodrugs, chemotherapeutic agents, small molecules, and combinations thereof.

The active agents may be stored in the silk blend film or silk spheres of the present invention for a long period of time. For example, the long-term storage of the active agents in the silk medium of the invention may be five months, seven months, ten months or longer. In addition, the stability of the active agents in silk blend film or silk spheres is not significantly influenced by storage temperatures. For example, the active agents may retain significant activity even when being stored at 37° C., and in some cases may not lose any activity. In one embodiment, when an enzyme, such as a glucose oxidase, is stored in the silk blend film, the enzyme can maintain 100% enzymatic activity for at least ten months at room temperature, or even at 37° C.

The present invention provides for a new aqueous-based fabrication method for preparing silk spheres with controllable size and shape. The method was based on the phase separation between PVA and silk fibroin at a final weight ratio of silk/PVA in the blend solution at about 20/80. The method of obtaining the water-insoluble silk spheres comprises the steps of (a) air-drying the blend silk/PVA solution into a film; (b) dissolving the film in water; and (c) removing of residual PVA by subsequent centrifugation. The resulting silk spheres had a broad size distribution ranging from 300 nm up to 20 µm, and has an approximately 30%β-sheet content, and less than 5% residual PVA. The sphere shape can be changed by applying constraints on the silk/PVA blend film before dissolving it in water. For example, spindle-shaped silk spheres were obtained by simply stretching the blend film before dissolving it in water. The sphere size and polydispersity can be controlled either by changing the concentrations of silk and PVA, due to the change of silk-PVA intermolecular interaction, or by applying ultrasonication on the blend solution, due to the size reduction induced by mechanical forces. Drug loading in the silk spheres of the present invention was obtained by mixing model drugs in the silk fibroin solution before blending with PVA, and following the same steps of preparing the silk spheres. The distribution and loading efficiency of the drug molecules in silk spheres depended on their hydrophobic and charged nature, thus resulting in different drug release profiles. The whole fabrication procedure can be finished within one day. The chemical used in the fabrication process, PVA, is an FDA-approved ingredient in drug formulations. The silk micro- and nanospheres prepared in the present invention can serve as drug delivery carriers in a variety of biomedical applications.

Particular embodiments of the invention are described in non-limiting examples.

The present invention may be as defined in any one of the following numbered paragraphs:

1. A method of preparing silk spheres with the size of the spheres ranging from nanometers to micrometers, comprising:
   (a) mixing an aqueous silk fibroin solution with an aqueous PVA solution;
   (b) drying the solution of step (a) to form a film;
   (c) dissolving the film in water; and
   (d) removing at least a portion of the PVA, thereby forming silk spheres with the size of the spheres ranging from nanometers to micrometers.

2. A method of preparing silk spheres with the size of the spheres ranging from nanometers to micrometers, comprising:
   a. mixing an aqueous silk fibroin solution with an aqueous PVA solution to form a blend solution, wherein the PVA having an average molecular weight of 30,000-124,000, and wherein the concentration of silk in the blend solution is less than or equal to about 15 wt %, and the concentration ratio of silk:PVA ranges from about 1:1 to about 1:4;
b. drying the blend solution to form a film;
c. dissolving the film in water; and
d. removing at least a portion of the PVA, thereby forming the silk spheres with the size of the spheres ranging from nanometers to micrometers.

3. The method of paragraph 1 or 2, further comprising applying constraints on the silk/PVA blend film before dissolving the film in water to change the shape of the silk spheres.

4. The method of paragraphs 1-3, further comprising stretching the silk/PVA blend film before dissolving the film in water, thereby forming a spindle-shaped silk sphere.

5. The method of paragraphs 1-4, further comprising water-annealing the silk/PVA blend film before dissolving the film in water, thereby forming a disk-shaped silk sphere.

6. The method of paragraphs 1-5, wherein the size of the silk spheres is controlled by adjusting one or more of (a) the weight ratio of silk fibroin and PVA in the blend solution, (b) the concentrations of silk fibroin and PVA in the blend solution; (c) molecular weight of PVA; or (d) energy output of sonification applied on the silk/PVA blend solution before drying the solution to form a film.

7. The method of paragraph 1 or 2, wherein the sphere size is controlled by one or more of (a) adding glycerin or other hydroxyl groups-rich compounds or polymers in the silk/PVA blend solution; (b) adjusting pH of the silk/PVA blend solution; or (c) adding salt to the silk/PVA blend solution and optionally adjusting the salt concentration.

8. A method of preparing silk microspheres with the size of the spheres ranging from about 1 μm to about 30 μm comprising:
a. mixing an aqueous silk fibroin solution with an aqueous PVA solution to form a blend solution, wherein the PVA has an average molecular weight of 30,000-124,000, and wherein the concentration of silk in the blend solution is from about 0.02% to about 15 wt %, and the concentration ratio of silk:PVA ranges from about 1:1 to about 1:4.
b. drying the blend solution to form a film;
c. dissolving the film in water; and
d. removing at least a portion of the PVA, thereby forming the silk microspheres.

9. The method of paragraph 8, wherein the concentration of silk in the blend solution ranges from about 0.2% to about 5 wt %.

10. The method of paragraph 8 or 9, further comprising sonicating the blend solution before drying the solution to film, thereby forming silk microspheres with a size ranging from 5 μm to 10 μm.

11. The method of paragraphs 8-10, wherein the energy output of the sonication is no less than about 4 watts.

12. The method of any one of paragraphs 8-11, further comprising the steps selected from the group consisting of filtration, centrifugation, or combination thereof, thereby removing spheres smaller than 1 μm or 5 μm.

13. A silk fibroin microsphere composition, prepared according to the method of any one of paragraphs 8-12.

14. A method of preparing silk nano spheres with the mean sphere size of the nano spheres less than 500 nm, the PDI below 0.3, and no spheres larger than 2 μm, comprising:
a. mixing an aqueous silk fibroin solution with an aqueous PVA solution to form a blend solution, wherein the PVA has an average molecular weight of 30,000-124,000, and wherein the concentration of silk in the blend solution is up to about 0.2 wt %, and the concentration of PVA is up to about 0.8 wt %;
b. drying the blend solution to form a film;
c. dissolving the film in water; and
d. removing at least a portion of the PVA, thereby forming the silk nanospheres.

15. The method of paragraph 14, wherein the concentration of silk in the blend solution is up to about 0.04 wt %, and the concentration of PVA is up to about 0.16 wt %.

16. A method of preparing silk nanospheres with the mean sphere size of the nanospheres less than 330 nm, the PDI below 0.4, and no spheres larger than 2 μm, comprising:
a. mixing an aqueous silk fibroin solution with an aqueous PVA solution, wherein the PVA has an average molecular weight of 30,000-124,000, to form a blend solution, wherein the concentration of silk in the blend solution is up to 15 wt %, and the concentration ratio of silk and PVA is up to 1:4;
b. sonicating the blend solution;
c. drying the sonicated solution to form a film;
d. dissolving the film in water; and
e. removing at least a portion of the PVA, thereby forming the silk nanospheres.

17. The method of paragraph 16, wherein the energy output of the sonication is no less than about 8 watts.

18. The method of paragraph 16 or 17, further comprising the steps selected from the group consisting of filtration, centrifugation, or combination thereof, thereby removing spheres larger than 330 nm or 500 nm.

19. A silk fibroin nanosphere composition, prepared according to the method of any one of paragraphs 14-18.

20. A method of encapsulating an active agent in porous silk spheres with the size of the spheres ranging from nanometers to micrometers, comprising:
a. mixing an aqueous silk fibroin solution and an active agent with an aqueous polyvinyl alcohol (PVA) solution;
b. drying the solution of step (a) to form a film;
c. dissolving the film in water; and
d. removing at least a portion of the PVA, thereby forming the active agent encapsulated silk spheres.

21. The method of paragraph 20, wherein the active agent is selected from the group consisting of chemicals, proteins, peptides, nucleic acids, nucleic acid analogues, nucleotides, oligonucleotides or sequences, peptide nucleic acids, aptamers, antibodies, hormones, hormone antagonists, growth factors or recombinant growth factors and fragments and variants thereof, cytokines, enzymes, antibiotics, viruses, antivirals, toxins, prodrugs, chemotherapeutic agents, small molecules, and combinations thereof.

22. A pharmaceutical composition comprising porous silk spheres encapsulating an active agent, prepared according to the method of paragraph 20 or 21.

23. A biodelivery system comprising porous silk spheres encapsulating an active agent, prepared according to the method of paragraph 20 or 21.

24. A drug delivery system comprising silk nanospheres that encapsulate an active agent.

EXAMPLES

Example 1

Silk Fibroin Purification

Polyvinyl alcohol (PVA, average mol wt 30,000-70,000), Rhodamine B, protease XIV, and all other chemicals were purchased from Sigma-Aldrich (St. Louis, Mo.); Tetramethylrhodamine conjugated bovine serum albumin (TMR-BSA) and Tetramethylrhodamine conjugated dextran (TMR-Dextran) were from Invitrogen (Carlsbad, Calif.). Ultrapure water from the Milli-Q® Ultrapure Water Purification Systems (Millipore, Billerica, Mass.) was used in all the examples.

Silk fibroin aqueous stock solutions were prepared as described previously. Sofia et al., 54 J. Biomed. Mater. Res. A 139-48 (2001). Briefly, cocoons of *B. mori* were boiled for 20 min in an aqueous solution of 0.02 M sodium carbonate, and then rinsed thoroughly with pure water. After drying, the extracted silk fibroin was dissolved in a 9.3 M LiBr solution at 60° C. for 4 hr, yielding a 20% (w/v) solution. The resulting solution was dialyzed against distilled water using Slide-A-Lyzer® 3.5K MWCO dialysis cassettes, (Pierce, Rockford, Ill.) for three days to remove the residual salt. The solution was optically clear after dialysis and was centrifuged twice at 10,000 rpm for 20 min to remove silk aggregates as well as debris from original cocoons. The final concentration of silk fibroin aqueous solution was approximately 8% (w/v). This concentration was determined by drying the solution with a known volume and weighing the residual solid. The 8% silk fibroin solution was stored at 4° C. and diluted with ultrapure water before use.

Example 2

Preparation of Silk/PVA Blend Films

Silk solutions having a concentration of 0.2 wt %, 1 wt %, and 5 wt % were prepared as starting solutions to be mixed with PVA solutions. PVA solutions having a concentration of 0.2 wt %, 1 wt %, and 5 wt % were also prepared as starting solutions to be mixed with silk solutions. Different volumes of silk and PVA solutions were gently mixed in a glass beaker. During mixing, the total mass of silk and PVA in the blend solution was kept constant. Silk/PVA blend solution having 1 wt % silk and 4 wt % PVA was prepared by mixing 1 ml of 5 wt % silk starting solution and 4 ml of 5 wt % PVA starting solution, so that the weight ratio of silk and PVA in the blend solution was 20/80 and the total mass of silk and PVA in the blend solution was 250 mg. Silk/PVA blend solution having 2.5 wt % silk and 2.5 wt % PVA was prepared by mixing 2.5 ml of 5 wt % silk starting solution with 2.5 ml of 5 wt % PVA starting solution, so that the weight ratio of silk and PVA in the blend solution was 50/50 and the total mass remained 250 mg.

When mixing 1 wt % silk starting solution and 1 wt % PVA starting solution to prepare a silk/PVA blend solution with 0.2 wt % silk and 0.8 wt % PVA or silk/PVA blend solution with 0.5 wt % silk and 0.5 wt % PVA, the volumes of silk and PVA starting solutions used for blending were increased 50 times than volumes used for mixing 5 wt % silk and 5 wt % PVA starting solutions, and the total mass of silk and PVA in the blend solution still remained 250 mg; and when mixing 0.02 wt % silk starting solution and 0.02 wt % PVA starting solution to prepare a silk/PVA blend solution with 0.004 wt % silk and 0.016 wt % PVA or a silk/PVA blend solution with 0.01 wt % silk and 0.01 wt % PVA, the volumes of silk and PVA starting solutions used for blending were increased 250 times than volumes used for mixing 5 wt % silk and 5 wt % PVA starting solutions, and the total mass of silk and PVA in the blend solution still remained 250 mg. After mixing, the solution was stirred at 150 rpm for 2 hr at room temperature. The final concentrations of silk and PVA in each silk/PVA blend solutions are shown in Table 2.

The resulting silk/PVA blend solutions were then transferred to open polystyrene petri dishes, where the blend solutions prepared from 5 wt % silk and 5 wt % PVA starting solutions were transferred to dishes with a size of 35 mm×10 mm; and blend solutions prepared from 1 wt % silk and 1 wt % PVA or 0.2 wt % silk and 0.2 wt % PVA starting solutions were transferred to dishes with a size of 100×15 mm. All dishes were placed in a fume hood to dry overnight. Normally, the blend solutions were dried out within 3 hr, forming films with a thickness of 70 μm-100 μm. The dried films were then peeled off and stored in a sealed container at room temperature before use.

To evaluate the sonication effect on the sizes of silk spheres, 1 ml of 5 wt % silk starting solution was mixed with 4 ml of 5 wt % PVA starting solution in a 15-ml conical tube. The blend solution was subjected to sonication using a Sonifiers® S-450D ultrasonic cell disruptor (Branson Ultrasonics Corp., Danbury, Conn.) at an energy output of 12% or 25% amplitude for 30 sec, similar to the conditions used in the silk gelation. Wang et al., 2008. The solution after sonication was immediately transferred to open size 100×15 mm petri dishes and dried overnight.

Example 3

Preparation of Silk Nano- and Microspheres

The dried silk/PVA blend films from one of the blend solutions, prepared according to Example 2, were dissolved in 30 ml of ultrapure water in a 50 ml centrifuge tube under 10 min of gentle shaking at room temperature. The tubes were centrifuged for 20 min in a Sorvall® High-Speed Centrifuge (Thermo Scientific, Waltham, Mass.) at 16,000 rpm, 4° C. The supernatant was carefully discarded and the pellets were suspended in 30 ml of ultrapure water and were centrifuged again. To disperse the clustered silk spheres, the precipitated final pellets were suspended in 2 ml of ultrapure water, sonicated at 1% amplitude for 15 sec with a Branson ultrasonic cell disruptor. The resulting silk micro- or nanosphere suspension was then used for further characterizations.

Example 4

Characterizations of Silk Nano- and Microspheres

Fourier Transform Infrared (FTIR) Spectroscopy

The silk spheres suspension in water, prepared according to Example 3, was lyophilized. The lyophilized powder was examined by a Bruker Equinox 55/S FTIR spectrometer (Bruker Optics Inc., Billerica, Mass.) or a JASCO FTIR 6200 Spectrometer (JASCO, Tokyo, Japan) equipped with a deuterated triglycine sulfate detector and a multiple-reflection, horizontal MIRacle™ ATR attachment (using a Germanium (Ge) crystal, Pike Tech., Madison, Wis.). Secondary structural components including random coils, α-helices, β-pleated sheets, and turns were evaluated using Fourier self-deconvolution (FSD) of the infrared absorbance spectra. Background measurements were taken on an empty cell and the background was subtracted from the reading of samples.

For each measurement, sixty-four scans were recorded in a wave number ranging from 400 $cm^{-1}$ to 4000 $cm^{-1}$, with a resolution of 4 $cm^{-1}$. FSD of the infrared spectra covering the amide I region (1595-1705 $cm^{-1}$) was performed by Opus 5.0 software (Opus Software, Inc. San Francisco, Calif.), as described. Hu et al., 39 Macromol. 6161-70 (2006). The absorption peaks at the frequency ranges of 1616 $cm^{-1}$-1637 $cm^{-1}$ and 1695-1705 $cm^{-1}$ correspond to the enriched β-sheet structure in silk II form; the absorption peaks at the frequency range of 1638 cm$^{-1}$-1655 cm$^{-1}$ ascribe to the random coil structure; the absorption peaks at the frequency range of 1656 cm$^{-1}$-1663 cm$^{-1}$ correspond to the α-helix structure; and the absorption peaks at the frequency range of 1663 cm$^{-1}$-1695 cm$^{-1}$ correspond to the turn structure. Hu et al., 2006.

Differential Scanning Calorimetry (DSC)

The dried silk/PVA blend films from one of the blend solutions, prepared according to Example 2, with a weight about 5 mg were loaded in aluminum pans, which were then heated in a TA Instrument Q100 DSC (TA Instruments, New Castle, Del.) with a dry nitrogen gas flow of 50 mL/min. Pure silk and pure PVA film served as a control. The instrument was calibrated for empty cell baseline and with indium for heat flow and temperature. Temperature-modulated differential scanning calorimetry (TMDSC) measurements were performed using a TA Instruments Q100, equipped with a refrigerated cooling system. The samples were heated at 2° C./min from −30° C. to 350° C. with a modulation period of 60 s and temperature amplitudes of 0.318° C.

Scanning Electron Microscopy (SEM) and Light Microscopy

One hundred (100) μl of the silk spheres suspension in water, prepared according to Example 3, was directly added on top of a conductive tape mounted on a SEM sample stub. The samples were dried overnight in the air and then sputtered with platinum. The morphologies of silk spheres were imaged using a Zeiss SUPRA™ 55VP SEM (Carl Zeiss SMT, Peabody, Mass.). For the light microscopy, the samples were prepared by either casting the blend film in a petri dish or loading 20 μl silk sphere suspension on top of a glass slide. The samples were placed under an inverted light microscope (Carl Zeiss, Jena, Germany). The images were taken with the installed software.

Dynamic Light Scattering (DLS)

DLS experiments were performed using a Brookhaven Instruments BI200-SM goniometer (Brookhaven Instruments Corp., Holtsville, N.Y.), equipped with a diode laser operated at a wavelength λ=532 nm. The temperature was kept at 25° C. with a 0.05° C. accuracy using a temperature-controlled recirculating bath. Scattered light intensity, I, and the time-averaged auto-correlation function (ACF) of the scattered intensity, $g_2(q,t)$, were measured simultaneously using a Brookhaven cross-correlator to prevent the after-pulsing effects at scattering angles (θ) ranging between 30° to 150°. The relaxation of density fluctuations at wave vector, q, and delay time, t, is probed through the equation:

$$g_2(q,t) = \frac{\langle I(t)I(0) \rangle}{\langle I \rangle^2},$$

where q relates to the refractive index of the solvent, n, through the equation:

$$q = \frac{4\pi n}{\lambda} \sin\left(\frac{\theta}{2}\right).$$

When the system is ergodic, i.e., when a time-averaged measurement of a property provides a good estimate of the ensemble average, $g_2(t)$ relates to the normalized field correlation function, $g_1(q,t)$, by the Siegert relation: $g_2(q,t)=1+A_2g_1(q,t)_2$, where A is the instrumental coherence factor. The 3rd order cumulant analysis was used to calculate the mean relaxation time, $\overline{\tau}_R$, and the polydispersity. The CONTIN method or exponential sampling was used to analyze the distribution of relaxation times. Using the cumulative analysis parameters, an assumed Gaussian hydrodynamic diameter probability density, G(Dh) and the hydrodynamic diameter cumulative distribution function, C(Dh) could be plotted for qualitative visualization and comparison of data. In these measurements, both CONTIN and exponential sampling gave similar particle size distributions.

Residual PVA Determination

During the preparation of silk spheres, the supernatant fractions from centrifugation were collected, and 1 ml of supernatant was diluted to 50 ml with ultrapure water. The diluted supernatants were subjected to the PVA determination. To determine the residual PVA content in silk spheres, the spheres were lyophilized, and then resuspended in 2 ml of freshly prepared protease XIV solution (1 mg/ml in PBS buffer, pH 7.4). The samples were incubated at 37° C. for 15 hr and the resulting solution was subjected to the PVA determination directly. The amount of PVA in solution was determined as described in the literature. Abdelwahed et al., 309 Int. J. Pharm. 178-88 (2006). Briefly, 0.5 ml of sample solution was mixed with 3 ml of 0.65 M boric acid solution and 0.5 ml of I$_2$/KI (0.05 M/0.25 M) solution, and the resulting solution was supplemented with ultrapure water to a volume of 10 ml. After 15 min of incubation at room temperature, the samples were subjected to absorbance measurement at 690 nm. The amount of PVA was calculated based on a standard curve generated at the same condition. The experiment was performed with N=3 for each data point. Statistical analysis was performed by one-way analysis of variance (ANOVA) and Student-New-man-Keuls Multiple Comparisons Test. Differences were considered significant when p≤0.05, and very significant when p≤0.01.

Example 5

Drug Loading in Silk Spheres

Drug Loading in Silk Spheres

Tetramethylrhodamine conjugated bovine serum albumin (TMR-BSA, M.w.=66,000 Da), tetramethylrhodamine conjugated dextran (TMR-Dextran, M.w.=10,000 Da), and rhodamine B (RhB, M.w.=479 Da) were used as model drugs to study the drug loading in silk nano- and micro spheres. Stock solutions of drugs were prepared with a concentration of 5 mg/ml in PBS buffer, pH 7.4, and stored at −20° C. Certain amount of stock solution of drugs was added to silk fibroin solution, before the silk fibroin solution was prepared into silk nano- and micro spheres, to reach to a drug/silk ratio of 1:100 (weight ratio). After mixing, the drug loaded silk fibroin solution was used to blend with PVA solution following the steps described in the Example 2, without the sonication treatment. A 5 wt % of silk and PVA concentrations and a silk/PVA ratio of 1:4 were used in this example. At this concentration, the silk/PVA film with a silk/PVA ratio of 1/4 can generate silk spheres with narrower size distribution, perhaps because the blend film is easier to dissolve in water forming homogeneous sphere suspension.

To determine the amount of drug loading in silk spheres, the supernatants collected from the centrifugation steps were subjected to absorbance measurement at 555 nm. The amount of drug was calculated based on a standard curve obtained at the same condition. The amount of drug in silk spheres was calculated from the difference between the total amount used and the amount remained in the supernatants. For each drug loading, at least three samples were prepared in order to obtain a standard deviation. The pellets from the last step of centrifugation were suspended in 2 ml of PBS buffer, pH 7.4, and used for the following confocal microscopy and drug release studies in Example 6.

Laser Scanning Confocal Microscopy

The distribution of drug molecules in silk microspheres was investigated by confocal microscopy. The drug-loaded silk spheres were prepared and resuspended in PBS buffer, as described above. A small portion of the suspension was imaged using a 63×, 1.4 N.A. water immersion lens on a Leica DM TRE2 microscope (Leica Microsystems, Wetzlar, Germany), at an excitation wavelength of 555 nm and emission wavelength of 580 nm. Single xy scans were collected for sphere size determination. Several xy scans with an optical slice of 1 μm were stacked along the z-direction to obtain a 3-D image, to visualize the pore structure of silk spheres or to evaluate the distribution of encapsulated drugs or proteins inside the spheres.

Example 6

Drug Release from Silk Spheres

Silk spheres loaded with model drugs as described in Example 5 were lyophilized. 10 mg of lyophilized silk spheres were suspended in 1 ml of PBS buffer, pH 7.4. The samples were incubated at room temperature under slow shaking condition. A cumulative drug release profile at each different time point (1, 4, 8.5, 24, 48, 120, 192, 342 hr) was determined by following the steps of (a) centrifuging the samples at 12,000 rpm for 10 min with a Sigma ISS-113 microcentrifuge (Sigma Chemical Co., St. Louis, Mo.); (b) carefully transferring the supernatants to empty tubes, subjecting the collected supernatants to the absorbance measurement at a wavelength of 555 nm, calculating the amount of model drug based on a standard curve, and comparing the data at the current time point with the original amounted drug loaded in the spheres; (c) suspending the precipitated pellets in 1 ml of PBS buffer; and (d) repeating the steps of (a)-(c) at each time point to obtain a cumulative drug release profile. For each model drug, at least three samples were prepared in order to obtain a standard deviation.

Example 7

Zeta Potential Measurement of Silk Spheres

Surface charges of the silk spheres were determined via Zeta potential measurements to explain drug loading and release properties of silk spheres loaded with different drugs. Silk spheres prepared from a silk/PVA (ratio of silk/PVA: 1/4) blend film were suspended in ultra pure water, yielding a concentration of about 100 μg/ml. One ml of the solution was then loaded to a zeta potential analyzer (Zetasizer nano, Malvern, Westborough, Mass.) for the zeta potential measurement at 25° C.

Example 8

Structural Characterization of Silk Sphere

To determine the beta-sheet content, FTIR was performed on both silk/PVA blend films (with a weight percentage ratio of silk/PVA in the blend films at 1:1 and 1:4, and herein referred to as 1/1 blend film and 1/4 blend film, respectively) prior to dissolution, and on the lyophilized silk spheres prepared from the same blend films followed with different treatments, such as direct dissolution, water vapor-treatment (water-annealing), and stretching.

As a high beta-sheet content control, the spheres prepared from methanol-treated silk/PVA blend solutions were also measured. It was found that the as-cast films initially exhibited a mostly amorphous structure (1538 $cm^{-1}$) with some silk I structure (1658, 1652 $cm^{-1}$). After water-annealing treatment, the silk I structure was predominant, while after methanol treatment the silk II content (1697, 1627, 1528 $cm^{-1}$) increased with the formation of more than 50% beta-sheet. Once significant amount of silk I structure (about 30% beta-sheet) formed, further methanol treatment could not convert the structure to silk II.

As shown in Table 4, silk spheres from the methanol-treated blend solution had approximately 50% beta-sheet (silk II), whereas those from directly dissolved blend films had about 30% beta-sheet content (silk I). The blend films prior to water dissolution, however, showed different beta-sheet contents. The 1/1 silk/PVA blend film showed a 27% silk beta-sheet content, similar to that measured for the spheres after film dissolution, while the 1/4 silk/PVA blend film had only 20% beta-sheet. Apparently, similar to the role of water vapor on silk films, PVA promoted the formation of the silk I structure in the 1/1 silk/PVA blend film, perhaps due to hydrogen bonding formed between hydroxyl groups of PVA and silk. In the case of the 1/4 silk/PVA blend film, the presence of PVA at high concentration may have restricted the silk structural transition from amorphous to silk I, due to more extensive hydrogen bonds formed between silk and PVA. During film dissolution, a decrease in local PVA concentration led to reduced hydrogen bonding between silk and PVA, and as a result, the transition from amorphous to silk I structure could occur.

Figure 8:
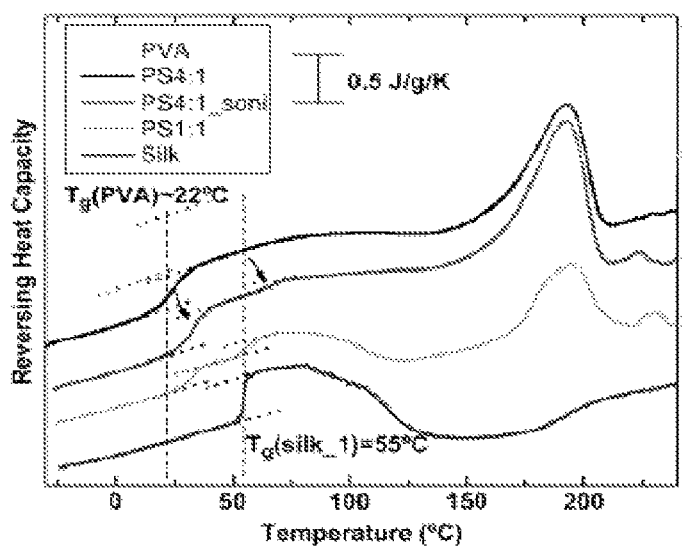
FIG. 8 depicts the results of differential scanning calorimetry (DSC) measurement on silk/PVA blend films. "PS" represents PVA and silk. For the blend film obtained by blending 1:1 of silk/PVA (weight ratio), the glass transition temperature (Tg) of PVA shifted toward higher temperature, while Tg of silk did not change. For the blend film obtained by blending 1:4 of silk/PVA (weight ratio), Tg for both PVA and silk did not change. For the silk/PVA 1/4 blend and sonicated film, Tg for both PVA and silk shifted toward higher temperatures. PVA and silk film alone served as a control.

The intermolecular interactions between silk and PVA in different blend films were demonstrated by the DSC data. As shown in FIG. 8, the glass transition temperatures (Tg) for silk and PVA in the 1/4 silk/PVA blend film did not significantly change when compared to the control samples, silk and PVA film alone (22° C. and 55° C., respectively). It was shown that the Tg of silk film is stable when bound water is plasticized in the sample. This indicates that the intermolecular interactions between silk and PVA, though restricting silk structural transitions as discussed above, did not significantly change the material properties for the PVA and silk separated phases in the blend film. For the 1/1 silk/PVA blend film, the silk Tg did not significantly change but the Tg for PVA shifted toward silk to 35° C., indicating that intermolecular interactions between silk and PVA reached a state such that PVA properties were changed. Meanwhile, the interaction also induced a silk structural transition to silk I, but not a significant shift in Tg, perhaps because the shift of the silk Tg only occurs only with silk TI (betasheets crystal) structure formation. Evidence was shown in the 1/4 silk/PVA blend and sonicated film, in which the Tg for PVA and silk component increased to 37° C. and 70° C., respectively. As revealed by FTIR, the beta-sheet content in the same film was 42%, much higher that the 19% content in the film without sonication.

TABLE 4

β-sheet content in the silk spheres prepared from the Silk/PVA blend film

| Sample | Silk/PVA ratio in silk/PVA blend film | Treatment | β-sheet content (%) |
|---|---|---|---|
| 1 | 1/4 | Dissolving the blend film in water | 30 |
| 2 | 1/4 | Stretching and dissolving the blend film in water | 28 |
| 3 | 1/4 | Water annealing and dissolving the blend film | 30 |

TABLE 4-continued

β-sheet content in the silk spheres
prepared from the Silk/PVA blend film

| Sample | Silk/PVA ratio in silk/PVA blend film | Treatment | β-sheet content (%) |
|---|---|---|---|
| 4 | 1/4 | Control: the blend film prior to dissolution | 19 |
|   | 1/4 | Sonicating the blend solution at 25% amplitude | 42 |
| 5 | 1/4 | Adding 50% MeOH added to the blend solution | 48 |
| 6 | 1/1 | Control: the blend film prior to dissolution | 27 |
|   | 1/1 | Dissolving the blend film in water | 28 |
| 7 | 1/1 | Stretching and dissolving the blend film in water | 30 |
| 8 | 1/1 | Water annealing and dissolving the blend film | 33 |

Example 9

Controlling the Size of Silk Spheres

To obtain more homogeneous micro- or nano spheres, different strategies were employed to control silk phase separation in PVA solution, for instance, dilution of silk fibroin and/or PVA to reduce the number of hydrogen bonds formed between silk and PVA; or sonication of the silk/PVA blend solution to break down large silk macro- or microphases via application of high energy to the blend system; or mixing the silk/PVA solution with another —OH rich compound, such as glycerin, to influence the interaction between PVA and silk, thereby influencing the phase separation.

The effect of varying polymer concentrations in silk/PVA blend solution on particle sizes was tested by dilution. The concentrations of initial silk solution and initial PVA solution in preparing blend solution were decreased progressively from 5 wt % to 1 wt % and 0.2 wt %, while keeping the weight ratio of silk and PVA in blend solution constant at 1/4.

Under SEM, there was no significant improvement for the 5 wt % and 1 wt % samples, while the 0.2 wt % sample was dominated by nanospheres with a relatively homogeneous size distribution (100-500 nm), as shown in FIG. 3.

To observe the in situ particle size in the hydrated state, samples were subjected to DLS. Prior to DLS measurements, silk sphere suspensions in water were filtered through a 5 mm membrane. FIG. 9A compares the sphere hydrodynamic diameter distributions (as probability densities, $G(D_h)$ and cumulative distribution functions, $C(D_h)$) obtained using the cumulative analysis for easy comparison of data collected from 5 wt % and 0.2 wt % preparations. FIG. 9B provides more quantitative size distributions obtained using exponential sampling (CONTIN analysis results gave similar diameter distributions and therefore not plotted for ease of visualization) for the same samples as in FIG. 9A. Cumulative analysis of DLS data collected from the 0.2 wt % sample showed a relatively homogeneous size distribution with a mean sphere size of 452 nm, and a polydispersity index (PDI) of 0.29, with no apparent sphere size larger than 2 mm. The 1 wt % and 5 wt % samples had larger mean sizes (536 and 578 nm, respectively) and PDI values (0.56 and 0.68, respectively), and a broad sphere size distribution ranging from 100 nm to 5 mm. The average sphere hydrodynamic diameters and polydispersities obtained using DLS cumulant analysis are summarized in Table 5. These results are consistent with the SEM data, confirming a decrease in the average particle size with decreasing concentration.

The DLS and SEM data demonstrated that the formation of hydrogen bonding between silk and PVA hydroxyl groups could stabilize silk spheres, while changing the polymer concentrations could alter silk/PVA interactions, and thus control average sphere size and size distribution.

Figure 9:
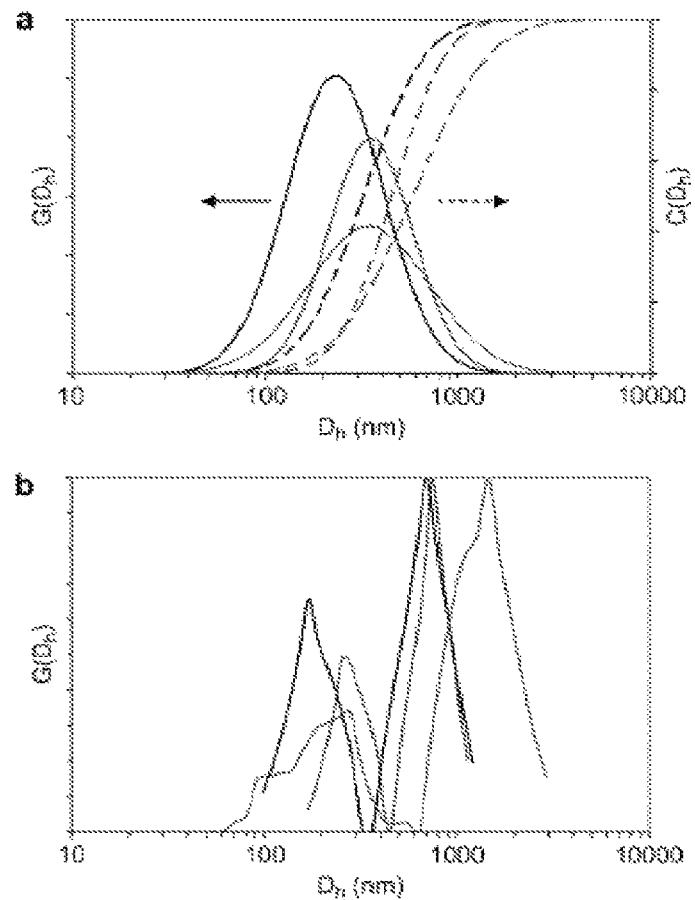
FIGS. 9A and 9B show the dynamic light scattering (DSL) measurements of silk spheres, where the size of the spheres was controlled by varying concentrations of silk and PVA in the silk/PVA blend solution silk, with the blended solution sonicated at 8 W sonication energy.

The solution was subjected to ultrasonication prior to film casting to demonstrate the effect of energy input on silk/PVA phase separation. The concentrations of initial silk solution and initial PVA solution in preparing blend solution were 5 wt % the weight ratio of silk and PVA in blend solution at 1/4. When 12% and 25% of maximal sonication energy output (corresponding to 4 and 8 watts, respectively) were used, light microscopy indicated that the cast silk/PVA blend films were dominated by microspheres and nanospheres, respectively (FIG. 9). The 12% amplitude energy output can break down larger microspheres, resulting in smaller microspheres with a size range of 5-10 mm. The 25% amplitude energy was high enough to break most spheres (including smaller spheres clusters) down to nanometer size.

DLS measurements confirmed the light microscopy observations and provided additional information about the presence of nanospheres in sonicated samples. FIGS. 9A and 9B show cumulant and exponential sampling results obtained from 25% amplitude sonicated samples, with different concentrations of silk and/or PVA in silk/PVA blend solution. Cumulant analysis of DLS data collected from the 25% amplitude treated samples showed a mean sphere size of 322 nm, a PDI of 0.4, and no spheres larger than 2 mm. The 12% amplitude sample also contained similar sized nanospheres, but the static light scattering intensity was approximately 4 times lower than that of the 25% amplitude sample. Considering the same initial silk/PVA concentrations were used prior to sonication, the lower scattered intensity from the 12% amplitude sample when compared to the 25% amplitude sample was attributable to the filtering of several-micron-sized spheres observed by light microscopy during DLS sample preparation of 12% sonicated samples. Therefore, changing sonication energy output, i.e., energy input in the blend solution, can effectively control the average size and size distribution of silk spheres covering both micro- and nanometer ranges.

The beta-sheet content in the silk spheres prepared by 25% amplitude sonication was determined by FTIR. The result showed a significant increase of betasheet formation, approximately 12%, when compared to the silk spheres without sonication treatment, indicating the formation of crystal silk II structure in this case (Table 4). The sonicated silk in the blend film prior to dissolution showed a low beta-sheet content, 19%, similar to that in the as-cast film and silk solution, indicating that the crystal silk II structure formation may occurred during the film dissolution process, but not during or after sonication and film drying. Similar to that observed in the silk/PVA 1/4 film without sonication, the strong intermolecular interactions between silk and PVA during sonication also restricted the silk structural transition from amorphous to silk II structure. The intermolecular interactions in this case were more extensive and stronger, so that the $T_g$ for both silk and PVA shifted toward higher temperatures, as revealed by DSC measurement (FIG. 8).

TABLE 5

Average sphere hydrodynamic diameters and polydispersities obtained using DLS cumulant analysis.

| Silk/PVA Concentration (wt %) | Sonication amplitude(%)/ Time(s) | $D_h$ (nm) | PDI (a.u.) |
|---|---|---|---|
| 5 | None | 578 | 0.68 |
| 1 | None | 536 | 0.56 |
| 0.2 | None | 452 | 0.29 |
| 5 | 12/30 | 308 | 0.4 |
| 5 | 25/30 | 322 | 0.4 |

Example 10

Yield and Stability of Silk Spheres

The yield of silk nano- and microspheres prepared from silk/PVA blend solution containing weight percentage ratio of silk/PVA at 1/4 was estimated based on the mass balance after lyophilization. The yield was about 50-60% for the 25% amplitude-sonicated sample, 30-40% for the 12% amplitude-sonicated sample and less than 20% for the non-sonicated sample.

The stability of the sphere suspension, as observed during sample storage at 4° C. for up to 3 months, followed a similar trend to the yield, with the 25% amplitude-sonicated sample more stable than the others. Although a small portion of nanospheres in the 25% amplitude-sonicated sample precipitated during storage, they could be readily re-suspended by shaking. The microspheres in the 12% amplitude-sonicated and non-sonicated sample, however, precipitated within a few days, forming a dense pellet. After being stored for more than a week, the samples had to be sonicated again to obtain individual microspheres. It is likely the silk spheres prepared under different sonication conditions had different mechanical properties, due to the beta-sheet contents in the spheres, resulting in different yields and stability.

We claim:

1. A method of preparing silk spheres with the size of silk spheres ranging from nanometers to micrometers, comprising:
    (a) mixing an aqueous silk fibroin solution with an aqueous PVA solution;
    (b) drying the solution of step (a) to form a silk/PVA blend film;
    (c) dissolving the silk/PVA blend film in water; and
    (d) removing at least a portion of the PVA, thereby forming silk spheres with the size of the silk spheres ranging from nanometers to micrometers.

2. The method of claim 1 further comprising applying constraints on the silk/PVA blend film before dissolving the silk/PVA blend film in water to change the shape of the silk spheres.

3. The method of claim 1 further comprising stretching the silk/PVA blend film before dissolving the film in water, thereby forming a spindle-shaped silk sphere.

4. The method of claim 1 further comprising water-annealing the silk/PVA blend film before dissolving the film in water, thereby forming a disk-shaped silk sphere.

5. The method of claim 1 further comprising controlling the silk sphere size, wherein the size of the silk spheres is controlled by adjusting one or more of
    (a) the weight ratio of silk fibroin and PVA in the silk/PVA blend solution;
    (b) the concentrations of silk fibroin and PVA in the silk/PVA blend solution;
    (c) molecular weight of PVA in the silk/PVA blend solution; or
    (d) energy output of sonication applied to the silk/PVA blend solution before drying the silk/PVA blend solution to form the silk/PVA blend film.

6. The method of claim 1 further comprising controlling the silk sphere size, wherein the silk sphere size is controlled by one or more of
    (a) adding glycerin or other hydroxyl groups-rich compounds or polymers to the silk/PVA blend solution;
    (b) adjusting the pH of the silk/PVA blend solution; or
    (c) adding salt to the silk/PVA blend solution.

7. A method of preparing silk microspheres with the size of the silk spheres ranging from 1 μm to about 30 μm comprising:
    a. mixing an aqueous silk fibroin solution with an aqueous PVA solution to form a silk/PVA blend solution, wherein the PVA has an average molecular weight of 30,000-124,000, and wherein the concentration of silk in the silk/PVA blend solution is from about 0.02% to about 15 wt %, and the concentration ratio of silk:PVA ranges from about 1:1 to about 1:4;
    b. drying the silk/PVA blend solution to form a silk/PVA blend film;
    c. dissolving the silk/PVA blend film in water; and
    d. removing at least a portion of the PVA, thereby forming the silk microspheres.

8. The method of claim 7, wherein the concentration of silk in the silk/PVA blend solution ranges from about 0.2% to about 5 wt %.

9. The method of claim 7 further comprising sonicating the silk/PVA blend solution before drying the solution to film, thereby forming silk microspheres with a size ranging from 5 μm to 10 μm.

10. The method of claim 9, wherein the energy output of the sonication is no less than 4 watts.

11. The method of claim 7, further comprising the steps selected from the group consisting of filtration, centrifugation, or combination thereof, thereby removing spheres smaller than 1 μm or 5 μm.

12. A method of preparing silk nanospheres with the mean sphere size of the silk nanospheres less than 500 nm, the PDI below 0.3, and no spheres larger than 2 μm, comprising:
    a. mixing an aqueous silk fibroin solution with an aqueous PVA solution to form a silk/PVA blend solution, wherein the PVA has an average molecular weight of 30,000-124,000, and wherein the concentration of silk in the silk/PVA blend solution is up to about 0.2 wt %, and the concentration of PVA is up to about 0.8 wt %;
    b. drying the silk/PVA blend solution to form a silk/PVA blend film;
    c. dissolving the silk/PVA blend film in water; and
    d. removing at least of portion of the PVA, thereby forming the silk nanospheres.

13. The method of claim 12, wherein the concentration of silk in the silk/PVA blend solution is up to about 0.04 wt %, and the concentration of PVA is up to about 0.16 wt %.

14. A method of preparing silk nanospheres with the mean sphere size of the silk nanospheres less than 330 nm, the PDI below 0.4, and no spheres larger than 2 μm, comprising:
    a. mixing an aqueous silk fibroin solution with an aqueous PVA solution to form a silk/PVA blend solution, wherein the PVA has an average molecular weight of 30,000-124,000, wherein the concentration of silk in the silk/

PVA blend solution is up to 15 wt %, and the concentration ratio of silk and PVA is up to 1:4;
b. sonicating the silk/PVA blend solution;
c. drying the sonicated solution to form a silk/PVA blend film;
d. dissolving the silk/PVA blend film in water; and
e. removing at least a portion of the PVA, thereby forming the silk nanospheres.

15. The method of claim 14, wherein the energy output of the sonication is no less than about 8 watts.

16. The method of claim 14 further comprising the steps selected from the group consisting of filtration, centrifugation, or combination thereof, thereby removing silk nanospheres larger than 330 nm or 500 nm.

17. A method of encapsulating an active agent in porous silk spheres with the size of the silk spheres ranging from nanometers to micrometers, comprising:
a. mixing an aqueous silk fibroin solution and an active agent with an aqueous polyvinyl alcohol (PVA) solution;
b. drying the solution of step (a) to form a silk/PVA blend film;
c. dissolving the film in water; and
d. removing at least a portion of the PVA, thereby forming the active agent encapsulating silk spheres.

18. The method of claim 17, wherein the active agent is selected from the group consisting of chemicals, proteins, peptides, nucleic acids, nucleic acid analogues, nucleotides, oligonucleotides or sequences, peptide nucleic acids, aptamers, antibodies, hormones, hormone antagonists, growth factors or recombinant growth factors and fragments and variants thereof, cytokines, enzymes, antibiotics, viruses, antivirals, toxins, prodrugs, chemotherapeutic agents, small molecules, and combinations thereof.

* * * * *